United States Patent
Jones et al.

(10) Patent No.: US 11,607,499 B2
(45) Date of Patent: Mar. 21, 2023

(54) DRUG DELIVERY DEVICE

(71) Applicant: SANOFI, Paris (FR)

(72) Inventors: Matthew Meredith Jones, Warwick (GB); William Geoffrey Arthur Marsh, Warwick (GB)

(73) Assignee: Sanofi, Paris (FR)

( * ) Notice: Subject to any disclaimer, the term of this patent is extended or adjusted under 35 U.S.C. 154(b) by 278 days.

(21) Appl. No.: 16/642,647

(22) PCT Filed: Sep. 13, 2018

(86) PCT No.: PCT/EP2018/074693
§ 371 (c)(1),
(2) Date: Feb. 27, 2020

(87) PCT Pub. No.: WO2019/053100
PCT Pub. Date: Mar. 21, 2019

(65) Prior Publication Data
US 2021/0154414 A1 May 27, 2021

(30) Foreign Application Priority Data
Sep. 15, 2017 (EP) ..................................... 17306191

(51) Int. Cl.
*A61M 5/315* (2006.01)
*A61M 5/31* (2006.01)

(52) U.S. Cl.
CPC ...... *A61M 5/31551* (2013.01); *A61M 5/3157* (2013.01); *A61M 5/31541* (2013.01); *A61M 5/31583* (2013.01); *A61M 2005/3126* (2013.01)

(58) Field of Classification Search
CPC .......... A61M 5/31551; A61M 5/31541; A61M 5/3157; A61M 5/31583; A61M 5/3155; A61M 5/20; A61M 2005/3126
See application file for complete search history.

(56) References Cited

U.S. PATENT DOCUMENTS

2016/0317745 A1   11/2016   Kjeldsen et al.

FOREIGN PATENT DOCUMENTS

| CN | 201431678 | 3/2010 |
|---|---|---|
| CN | 103037922 | 4/2013 |

(Continued)

OTHER PUBLICATIONS

International Preliminary Report on Patentability in Application No. PCT/EP2018/074693, dated Mar. 17, 2020, 9 pages.

(Continued)

*Primary Examiner* — Tasnim Mehjabin Ahmed
(74) *Attorney, Agent, or Firm* — Fish & Richardson P.C.

(57) ABSTRACT

The disclosure relates to a drug delivery device for expelling a pre-determined or pre-settable amount of a liquid medicament formulation which improves the stalling behavior and indicates the stalling state to the user. The device comprises:
a medicament reservoir attached to a housing and
an expelling mechanism configured for acting against the medicament reservoir in order to expel a portion of the liquid medicament formulation therefrom, the expelling mechanism comprising
an arrangement of a threaded nut in a fixed axial relation to the housing and a lead screw in threaded engagement with the threaded nut, the threaded nut and the lead screw being rotatable relative to each other by a rotational input interface,
a mechanical energy reservoir (for storing energy, the stored energy being releasable from the energy reservoir by a rotational interface,
a drive train having upstream and downstream interfaces; and
a trigger movable relative to the housing.

20 Claims, 12 Drawing Sheets

(56) References Cited

FOREIGN PATENT DOCUMENTS

| CN | 106659848 | 5/2017 | | |
|---|---|---|---|---|
| JP | 2016-514593 | 5/2016 | | |
| JP | 2017-520371 | 7/2017 | | |
| JP | 2017-521191 | 8/2017 | | |
| WO | WO 2011/152772 | 12/2011 | | |
| WO | WO 2014/166899 | 10/2014 | | |
| WO | WO 2015/032775 | 3/2015 | | |
| WO | WO 2015/091818 | 6/2015 | | |
| WO | WO 2016/001300 | 1/2016 | | |
| WO | WO 2016/012278 | 1/2016 | | |
| WO | WO-2016001300 A1 * | 1/2016 | .............. | A61M 5/20 |
| WO | WO 2016/154427 | 9/2016 | | |

OTHER PUBLICATIONS

International Search Report and Written Opinion in Application No. PCT/EP2018/074693, dated Nov. 22, 2018, 11 pages.

* cited by examiner

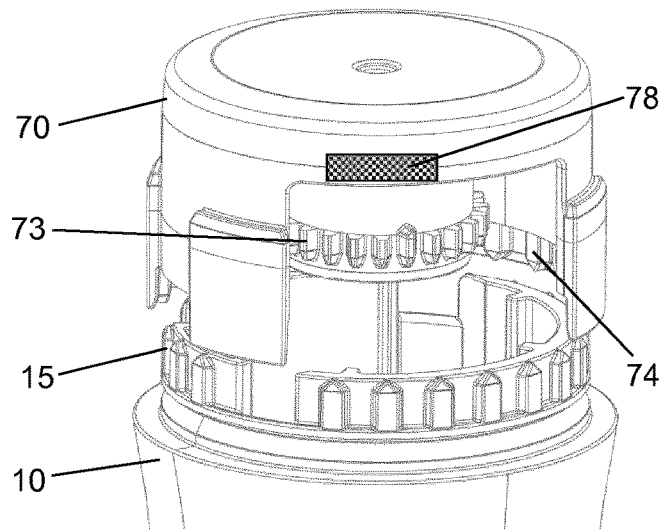
Fig. 6
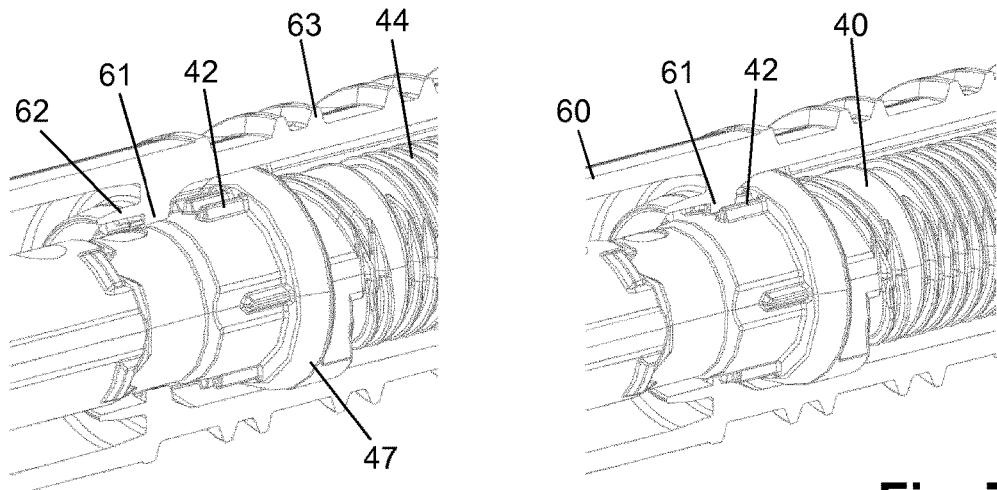
Fig. 7a
Fig. 7b
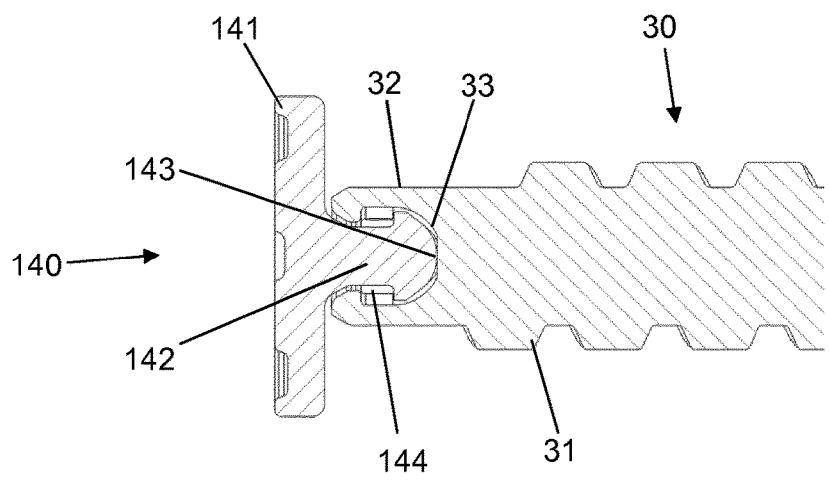
Fig. 8

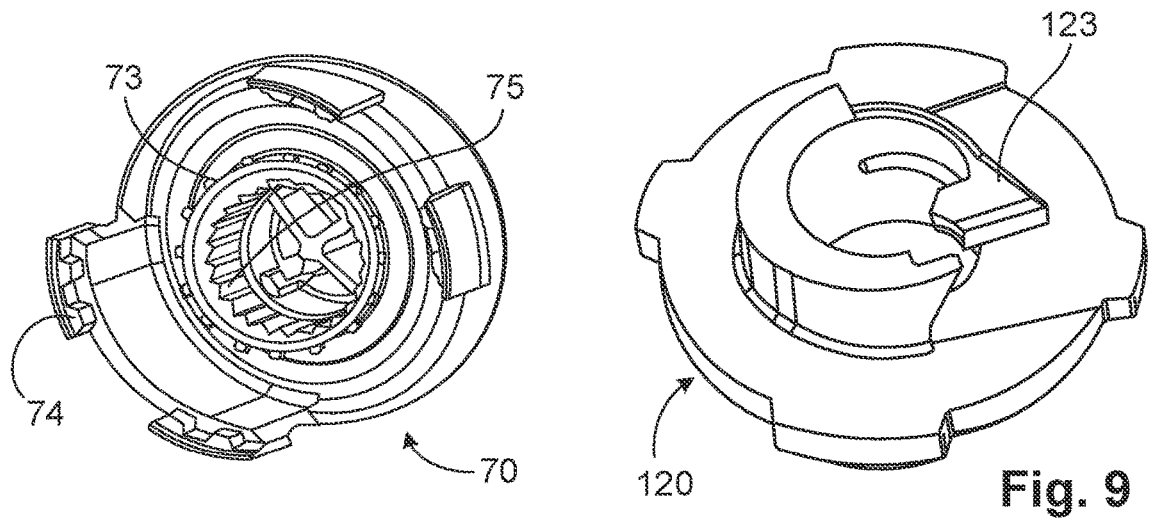
Fig. 9
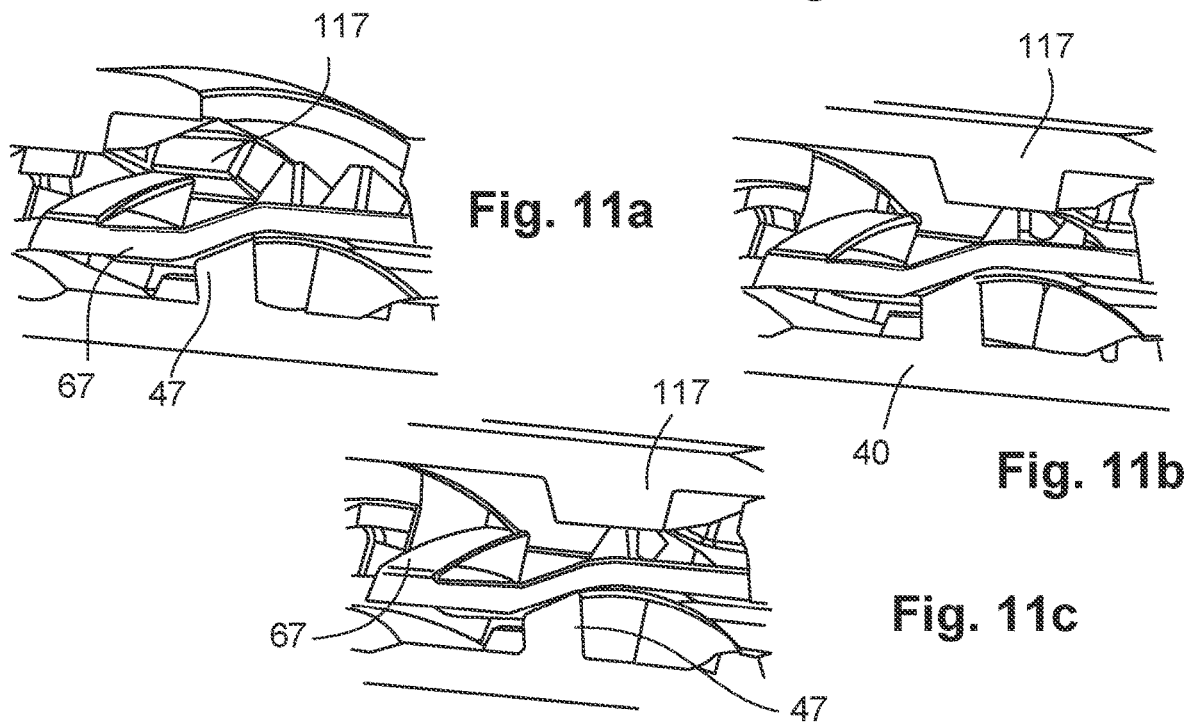
Fig. 10
Fig. 11a
Fig. 11b
Fig. 11c

DRUG DELIVERY DEVICE

CROSS REFERENCE TO RELATED APPLICATIONS

The present application is the national stage entry of International Patent Application No. PCT/EP2018/074693, filed on Sep. 13, 2018, and claims priority to Application No. EP 17306191.2, filed on Sep. 15, 2017, the disclosures of which are incorporated herein by reference.

TECHNICAL FIELD

The disclosure relates to a drug delivery device for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure may be applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or lead screw contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button (trigger), devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

The spring assisted devices often use a preloaded and/or user-loaded torsion spring (drive spring) in order to provide the necessary force (i.e. a torque) to drive the drive mechanism for dispensing the medicament dose. In this type of drug delivery devices the torque of the drive spring is transferred to the drive train of the drive mechanism and via the drive train which transfers the torque into a linear movement driving the bung of the cartridge for medicament dispensing from the cartridge through a needle connected to the cartridge. During normal conditions the full amount of torque provided by the drive spring is released as medicament fluid continues to be dispensed from the needle until the device reaches an equilibrium state which is a low stress state.

However, under certain circumstances, for example, if the needle is blocked, stalling occurs. Stalling is when a mechanism cannot fully relieve the mechanical energy stored in the wind-up system and in internal drive train strain within the predetermined time period of release button actuation for injection, which means injection time and holding time after injection (e.g. 30 seconds). There are two different types of stalling behaviour, namely obvious stalling and hidden stalling. The stalling is called obvious stalling if the drive mechanism stops before producing feedback indicative for correct completion of injection, whereas hidden stalling is defined such that the drive mechanism produces feedback indicative for completion of injection without fully relieving internal strain and hence without fully dispensing the dose. If, for example, users are instructed by the information for use to observe the entire return of the dose dial display to the "0" marking in order to correctly determine the end of the expelling operation, a hidden stalling condition may occur when the mechanism remains in a strained state exactly at that point. The effect of the strain is a backlash in the parts of the drive train that are downstream relative to the dose dial display. The extent of the backlash clearly corresponds to the elasticity of the strained drive train portion and, especially for small doses, may result in a considerable underdose. Root causes of stalling are not limited to the injection device itself and thereby cannot be exhaustively addressed by mere mechanism improvements. For example, stalling may occur as the result of needle bending by inadequate handling of the device. As stalling cannot be avoided in all circumstances the mechanical layout of the device therefore should be at least such that any stalling conditions will become apparent to a normally attentive user. This ability of an injection device shall be denoted as a well-defined stalling behaviour.

In one example the torque from the drive spring is transferred from a drive sleeve to a lead screw (e.g. via corresponding spline features) and then to the body of the drug delivery device, where it is converted to a linear axial motion via a thread contact. The axial movement of the lead screw causes the bung of the cartridge to move and dispense fluid from the needle. In a normal dispense with a working needle, when the device reaches the 0 units stop, no further energy is released from the drive spring. The residual torsion due to deflection of the drive mechanism components is then released as fluid continues to be dispensed from the needle, until the device reaches the above mentioned equilibrium state. When the needle is blocked the torsion in the drive mechanism cannot be released because the lead screw cannot advance.

SUMMARY

An object of the present disclosure may be seen in providing an improved drug delivery device with regard to its stalling behaviour. Especially, it may be understood as an object of the present disclosure to provide a drug delivery device which indicates its state with regard to stalling to the user.

This object is solved by a drug delivery device according to claim 1.

In general, a drug delivery device for automatically expelling a pre-determined or pre-settable amount of a liquid medicament formulation is provided,
the device comprising
a medicament reservoir attached to a housing and
an expelling mechanism configured for linearly acting against the medicament reservoir (e.g. its bung) in order to expel a portion of the liquid drug formulation therefrom, the expelling mechanism comprising
an arrangement of a threaded nut in a fixed axial relation to the housing and a lead screw in threaded engagement with the threaded nut, the threaded nut and the lead screw being rotatable relative to each other by a rotational input interface,
a mechanical energy reservoir for storing energy, the stored energy being releasable from the energy reservoir by a rotational interface, for example for providing a driving torque and transferring the driving torque to the lead screw for rotation and axial movement relative to the housing,
a drive train, in one embodiment comprising a drive sleeve, having an upstream interface coupled to the rotational interface of the energy reservoir for feeding rotational energy into the drive train and a downstream interface coupled to the rotational input interface of the arrangement of the threaded nut and the lead screw for outputting rotational energy thereto to thereby rotate the lead screw and the threaded nut relative to each other, the drive train further being equipped with a releasable latch for preventing (i.e. in an initial position) transfer of rotational energy from the upstream interface to the downstream interface when actuated and for allowing transfer of rotational energy from the upstream interface to the downstream interface when released; and
a trigger, e.g. a button, movable by a user relative to the housing from a first position to a second position, the trigger being connected to the releasable latch for operating the releasable latch by manipulation of the trigger (e.g. by pressing, for example in order to release the releasable latch), the trigger further being biased (e.g. by a compression spring) towards the first position opposite to the second position corresponding to release of the releasable latch; wherein the drive train further includes a rotational strain sensing arrangement which is configured to convert rotational strain into an axial force or interlocking, the axial force or interlocking being applied to the trigger by a mechanical linkage to thereby prevent the trigger from returning to the first position until the rotational strain acting on the rotational strain sensing arrangement of the drive train reduces below a predetermined threshold value.

According to the above general disclosure the drug delivery device may implement an expelling mechanism that indicates its state with regard to stalling to the user by means of the position of the trigger when the releasable latch is released by the user. If the expelling mechanism allows the trigger to entirely return to its initial rest position (first position) which is different from the second position, for example with regard to the longitudinal axis of the drug delivery device, the user knows that there is no residual torsion within the drive mechanism. This behavior may be achieved by detecting the extent of the residual rotational strain in the drive train wherein the trigger to return to its initial rest position only if the rotational strain is or decreases below a predetermined threshold value. In contrast, the circumstance that the trigger is not or not fully returned to its first position is used to indicate to the user that there is a considerable amount of residual rotational strain (or torque) within the drive mechanism which is equivalent to a stalling condition.

In instances the first position of the trigger may be an extended position with regard to the housing and the second position may be a retracted position with regard to the housing. In another embodiment the first position is a retracted position and the second position is an extended position with regard to the housing. Thereby retracted means either fully or partly retracted with regard to the housing, for example with regard to the proximal end of the housing. In one embodiment the proximal end of the housing may be formed by a proximal end of a dose selector, e.g. a dose knob.

In one embodiment the mechanical linkage between the trigger and the rotational strain sensing arrangement is configured to allow the trigger to leave the second position under any torque strain condition and to move towards an intermediate position away from the second position thereby causing re-engagement of the releasable latch. The intermediate position is located between the first (initial) position and the second position.

In one embodiment the trigger is a button, which is axially pressed in distal direction for initiating dispensing of the selected dose. Alternatively, the trigger is a button which is axially pulled in proximal direction for initiating dispensing of the selected dose.

In a further embodiment the trigger is held in the second position during dispensing of the medicament dose and released or manually moved back by the user when the user finishes dose application. Sometimes, the user releases or manually moves back the trigger when only part of the dialed dose is applied. In one embodiment the expelling mechanism comprises a clutch spring which is adapted to drive the trigger from the second position to the first position after the user has released the trigger via the drive sleeve providing that the residual torsion is less than the predefined value.

In another embodiment concerning the power transmission from the mechanical energy reservoir to the lead screw the releasable latch is located between the upstream interface and the rotational strain sensing arrangement or, alternatively, the latch is located between the downstream interface and the rotational strain sensing arrangement. In the first case the trigger returned to the first position if the dispensing step is interrupted before the full pre-defined or dialed dose is expelled so that the residual rotational strain within the system is shown to the user. In the second case the trigger stayed in the second position (and did not return to the first position) even without stalling if the dispensing step is interrupted before the full pre-defined or dialed dose is expelled showing to the user that the pre-defined or dialed dose is not fully expelled.

In one embodiment the drive train comprises a releasable latch (or clutch mechanism) which is released or disengaged by the movement of the trigger from the first position to the second position in order to allow transfer of rotational energy from the upstream interface to the downstream interface and to dispense the selected dose of the medicament from the medicament reservoir. The latch may be reengaged if the trigger at least partly returns (i.e. returns at least part of the way) from the second position to the first position. The latch may be—accordingly—released or disengaged if the trigger at least partly returns (i.e. returns at least part of the way) from the second position to the first position, i.e. to an intermediate position.

In one embodiment the drive train may further include a user-settable end stop limiter, for example a dose knob, configured for enabling a user to restrict the amount of rotation that is transferred by the drive train upon release of the releasable latch to a user-determined angle. In this case the amount of liquid medicament formulation expelled during dose dispensing step initiated by the trigger may be selected by the user. For example, the mechanical energy reservoir (e.g. a torsion spring) is coupled to the end stop limiter such as to translate setting of the end stop limiter into immediate energizing of the energy reservoir to an extent corresponding to the rotational angle selected by the user. This embodiment realizes a wind up mechanism used, for example, during dose setting, which loads energy into the energy reservoir, which is sufficient and necessary for dispensing the set dose. Alternatively, the amount of rotation that is transferred to the drive train upon release of the releasable latch is pre-determined, for example by the pre-stressing of a torsion spring.

In one embodiment, which is cost-effective in realization, the drive train comprises a drive sleeve and the downstream interface of the drive train comprises a spline at the drive sleeve, the first splined connection formed by the spline and the rotational input interface being located at an axial distance relative to the treaded nut, wherein the rotational strain sensing arrangement includes a locking ring being maintained in a rotational fixed relation to the lead screw by a second splined connection at a position located between the first splined connection and the threaded nut, the locking ring and the drive sleeve implementing angular dependent axial keying to thereby limit relative axial travel between these parts when the advancing angle of the drive sleeve relative to the locking nut due to torsional deformation exceeds a predefined threshold angle.

In one embodiment the lead screw is flexible. In case that there is a residual rotational strain this rotational strain twists/distorts the lead screw due to its flexibility. Accordingly, the locking ring which is rotationally constrained to the lead screw is rotated about the same amount relative to the drive sleeve. The locking ring is splined to the lead screw and axially constrained to the housing. The relative rotation of the locking ring with regard to the drive sleeve is used to prevent movement of the drive sleeve in an axial direction and with it prevent movement of the trigger into the first position.

In a further embodiment the mechanical linkage between the trigger and the rotational strain sensing arrangement includes a mechanical connection that at least partly limits the travel of the trigger according to the limitation occurring in the angular dependent axial keying between the drive sleeve and the locking nut. In one embodiment the trigger is mechanically connected to an axial movement of the drive sleeve and/or the locking nut. This means that the connection between the trigger and the drive sleeve and/or the locking nut is such that an axial movement of the drive sleeve and/or the locking nut drives the trigger in axial direction. In one case the locking nut may be axially fixed to the housing but alternatively, the locking nut may be axially movable with regard to the housing.

In one embodiment the angular dependent axial keying comprises a slotted engagement of a radial pin rotationally fixed at the locking nut and the drive sleeve in an L-shaped track to thereby restrict relative axial travel between the locking nut and the drive sleeve according the relative angular position thereof.

In an alternative embodiment, if the lead screw is not (sufficiently) flexible, the drive sleeve comprises a flexible arm with a spline feature guided within an axial spline of the lead screw, wherein the rotational strain of the energy reservoir provided by the rotational interface deflects the flexible arm into a direction perpendicular to the axial direction, i.e. a tangential direction. Accordingly, the torsional deformation occurs in this case in the flexible arm. Analogously to the above embodiment, the first element is a locking ring rotationally constrained to the lead screw and the second element is the drive sleeve. In this embodiment the flexibility of the lead screw causing relative rotation of the lead screw and the drive sleeve is replaced by the flexibility of the arm of the drive sleeve guided within the axial spline of the lead screw. The flexible arm is elongated along the longitudinal direction of the device and the drive sleeve and may be twisted into a direction perpendicular to the longitudinal direction (tangential direction), for example around the circumference of the drive sleeve. In one embodiment the flexible arm may be formed by a respective cutout within the drive sleeve. The flexible arm is accommodated within the plane of the drive sleeve body, wherein the spline feature extends from the inner surface of the flexible arm.

With regard to both above embodiments, for example, the rotational strain sensing arrangement comprises a locking ring and a radial pin provided at the outer surface of the locking ring which is moved within a first axial section of an L-shaped track of the drive sleeve caused by the movement of the trigger relative to the housing, wherein the drive sleeve is axially coupled to the trigger during initiating dispensing of the selected dose. The radial pin of the locking ring is additionally moved within a second circumferential (tangential) section of the L-shaped path (e.g. slot) running perpendicular to the first section caused by the deflection caused by the rotational strain of the energy reservoir. The radial pin of the locking ring stays within the second circumferential section if the rotational strain is not released at the end of the dispensing step. Thereby, the return movement of the drive sleeve is prevented, so that the trigger is not forced into the initial position. In this embodiment, the connection between the drive train and the lead screw formed by the downstream interface and the rotational input interface, e.g. a splined connection, is located an appreciable distance from the locking ring radial pin.

In another embodiment, the second section of the L-shaped path of the drive sleeve allows a movement of the radial pin in an axial direction, for example by widening the second section of the L-shaped path in axial direction. This allows movement of the drive sleeve into the proximal direction if the radial pin is in the second section of the L-shaped track so that a releasable latch is reengaged thereby preventing transfer of rotational energy from the upstream interface to the downstream interface. Thereby, the user is allowed to interrupt the dispense action of the device part way through dispense by removing the force they applied to the trigger, but the trigger does not move fully back to its initial position, preferably to an intermediate position.

In one embodiment the strain sensing arrangement of the drive train comprises a helical interface for converting the rotational strain into an axial strain. For example, the helical interface may comprise a clutch plate having an outer spline and a proximal section of a number sleeve having an inner spline, wherein at least one of the outer spline and the inner spline has an angled surface or edge, wherein the clutch plate is axially coupled to the trigger.

In one embodiment the mechanical linkage between the strain sensing arrangement and the trigger is configured to feed an axial force produced by the strain sensing arrangement to the trigger to thereby compensate the biasing force until the rotational strain acting on the strain sensing arrangement of the drive train reduces below the predetermined threshold value. For example, the resulting axial load produced by the helical interface causes the clutch plate to held in the distal position and thereby prevents the clutch spring from returning the trigger to the first position even if the trigger is released by the user as long as the rotational strain does not reduce below the predetermined threshold value.

In this embodiment the proximal section of the number sleeve may form a separate element which is fixedly attached to the distal section of the number sleeve. Alternatively, the proximal and the distal part of the number sleeve are integrally formed. The inner spline of the number sleeve and the outer spline of the clutch plate run parallel to the longitudinal axis of the drug delivery device and one of the spline runs at least partially under a small angle (e.g. lower than or equal to 30°) to the longitudinal axis if the spline edge and the longitudinal axis are projected into a circumferential plane around the longitudinal axis of the drug delivery device. For example, the inner spline of the number sleeve and the outer spline of the clutch plate mesh with one another such that the clutch plate is clamped by the inner spline of the number sleeve as long as there is the above defined residual torque. When meshing with one another the clutch plate and the number sleeve rotate relative to one another. The clutch plate is, for example, a sleeve-like or ring-like component and clutched to the drive sleeve, preferably via a ratchet interface. Further, the clutch plate may provide a clicker arm for interaction with ratchet features of the trigger.

In another embodiment the angled surface or edge of the inner spline comprises an angled surface with a first inner spline section formed by the proximal section of the number sleeve and a second inner spline section formed by a distal section of the number sleeve. This embodiment allows the drive sleeve to move far enough to reengage the releasable latch if the user, for example, releases the trigger, causing the dose dispense to be interrupted. The second inner spline section may run parallel to the longitudinal axis of the drug delivery device, whereas the first inner spline section has a small angle (e.g. lower than or equal to 30°) to the longitudinal axis if the spline edge and the longitudinal axis are projected into a circumferential plane around the longitudinal axis of the drug delivery device.

In an embodiment mechanical energy reservoir may comprise a clutch spring which may be formed as a compression spring. Preferably, the clutch spring is located axially interposed between the stationary housing component and the axially movable drive sleeve. The sleeve may comprise latch features adapted to engage corresponding latch features of the releasable latch. Preferably, the latch forms a releasable ratchet clutch suitable to couple and de-couple the sleeve and the threaded nut. In another embodiment the latch features each form a series of teeth. In a preferred embodiment the clutch spring biases (actuates) the latch features into engagement. For example the latch features may be rotationally constrained when engaged and free to rotate relative to each other when released. The released state of the latch features may include a condition where the latch features contact each other, but are allowed to overhaul each other, i.e. the latch features slip. The axial position of the drive sleeve, clutch plate and trigger is defined by the action of the clutch spring, which applies a force on the drive sleeve in the proximal direction.

The latch features may be in a releasable engagement allowing the latch features to be overhauled against the bias of the clutch spring at least in one rotational direction when the sleeve is in the proximal position and that the latch features are rotationally constrained when the sleeve is in the distal position. For example, the latch features may each comprise a series of teeth, preferably saw-teeth, which are allowed to slip over each other if not pressed against each other too firmly. In other words, the latch features may be overhauled against the bias of the clutch spring by allowing the sleeve and/or the other latch element to translate axially against the force of the clutch spring. This may result in an oscillating axial movement of the sleeve and/or the latch element due to continued disengagement and following re-engagement into the next detent position. An audible click may be generated by this re-engagement, and tactile feedback may be given by the change in torque input required.

In addition, the latch features may comprise teeth having a ramp angle allowing overhauling of the ratchet, e.g. for dose correction when used in a drug delivery device. In other words, relative rotation of the sleeve and the clutch element is allowed in both directions when the spring arrangement is in the state or condition where the clutch features and the corresponding clutch features are not rotationally fixed.

Preferably, the latch features and the corresponding clutch features provides a detented position between the sleeve and the latch element corresponding to each dose unit when used in a drug delivery device, and engage different ramped tooth angles during clockwise and anti-clockwise relative rotation. This is especially useful if the spring arrangement further comprises a drive spring having a rotational force or torque which is reacted via the latch features and the corresponding latch features from the clutch element and the sleeve to the housing component.

The sleeve is preferably coupled (directly or indirectly) to the trigger (button) such that upon actuation of the trigger the sleeve is translated against the bias of the clutch spring from the first proximal position in which the sleeve is rotationally locked to the housing component into the second distal position in which the sleeve is rotationally unlocked from the housing component. In other words, there are two states of the sleeve, namely a state where the sleeve is rotationally locked to the housing component and a state where the sleeve is allowed to rotate relative to the housing component, which two states are defined by the axial position of the sleeve relative to the housing component. The sleeve is held in one of these states by the action of the clutch spring as long as the trigger is not actuated to displace the sleeve against the spring force. Preferably, upon release of the trigger the clutch spring translates the sleeve and the trigger into the proximal position.

The clutch spring may be a compression spring, preferably an axially acting compression spring. As an alternative, the clutch spring may be a tension spring. In instances the clutch spring may be a coil spring. As an alternative, the clutch spring may be a spring washer or a block or sleeve made from an elastically deformable material like rubber. Although the clutch spring is referred to herein as a single spring, the present disclosure shall be understood to encompass embodiments of the clutch spring with more than one single spring element as well. The spring elements, in instances, may be arranged in parallel or in series.

The latch element comprises latch features and may have the form of a plate or disk. As an alternative, the latch element may have the form of a sleeve. The latch element is axially interposed between the sleeve and the trigger such that axial movement of the trigger in a first direction, preferably in the distal direction, is transferred to the sleeve via the clutch element and axial movement in the opposite, preferably proximal, direction is transferred to the trigger via the clutch element. As an alternative, the latch element may be a unitary part of the trigger. In a preferred embodiment the clutch element is permanently or releasably coupled to further component parts of a drug delivery device, for example a number sleeve and/or a dose setting member. The latch element may be a multi-functional element having in addition to the interface with the sleeve and the interface with the trigger e.g. a clicker feature and/or at least one further interface.

The trigger is preferably a user operable element located proximally from the sleeve and the clutch element. When used in a drug delivery device, the trigger may extend from the proximal end of the device and, preferably, does not change its axial position during dose setting. The trigger is preferably coupled to a user operable dose setting member and may be releasably coupled to a number sleeve component and/or a stationary housing component. In an alternative embodiment, the trigger may be part of a dose setting arrangement or may be the dose setting member. The trigger may be a multi-functional element having in addition to the above features e.g. a clicker feature. In another embodiment the trigger and/or the dose selector may comprise a detent feature that was sufficient to resist the weight of the trigger but not sufficient to resist the force of the clutch spring (applied to the trigger via the drive sleeve and clutch plate). With this feature, the trigger would only return to its first position when driven by the drive sleeve (e.g. via the clutch plate) in an unblocked needle condition and not under the action of gravity.

The stationary housing is a fixed foundation for relative movements of the axially movable drive sleeve, the clutch element, the gauge element and the trigger and for relative rotational movements, e.g. of the number sleeve, the drive sleeve and the lead screw. It may be part of a multi-component housing or may be the only housing component of a drug delivery device. In a preferred embodiment, the housing comprises an axial support or bearing for the clutch spring and means for releasably engaging the sleeve. Preferably, the housing comprises one or more teeth, for example a ring of teeth, engaging one or more corresponding teeth, preferably also a ring of teeth, of the sleeve depending on the relative axial position of the sleeve with respect to the housing. In other words, the engagement means or teeth mesh and interlock in a first, e.g. proximal, position of the sleeve relative to the housing and are disengaged, thus allowing relative rotation, in a second, e.g. distal, position of the sleeve relative to the housing. The means for releasably engaging the sleeve, for example the ring of teeth, may be attached to a body insert which is a housing component fixedly attached to the housing. The housing may be a multi-functional element having in addition to the above features e.g. a clicker feature and/or an interface to a lead screw.

In one embodiment the drive train may comprise an axially movable drive sleeve which is a tubular element and has, preferably at its distal end, an interface for releasable engagement with the housing component and, preferably at its proximal end, an interface for releasable engagement with the releasable latch, namely latch features, for example a ring of radially extending outer teeth. In addition, the sleeve comprises an axial support or bearing for the clutch spring. The clutch spring may be arranged axially interposed between the housing component and the drive sleeve. In an alternative embodiment, the sleeve at least partly surrounds the clutch spring or the clutch spring at least partly surrounds the sleeve.

Preferably, the sleeve is a drive sleeve which is rotationally constrained to the lead screw, for example by a spline, which is in threaded engagement with the stationary housing part, e.g. the threaded nut. In other words, rotation of the drive sleeve relative to the housing component causes rotation of the lead screw and, thus, axial displacement of the lead screw relative to the housing component. This may be used in a drug delivery device during dose dispensing to advance a piston in a cartridge to expel medication from the cartridge. The sleeve may be a multi-functional element having in addition to the above features e.g. a clicker feature and/or an activation interface for a clicker.

A further aspect may be seen in the provision of several interfaces on the axially movable drive sleeve. Preferably, the drive sleeve has the upstream interface for permanently rotationally constraining the drive sleeve and the lead screw. An interface in form of the latch may be provided between the drive sleeve and the housing (or a housing component) for rotationally constraining the drive sleeve and the housing depending on the axial position of the drive sleeve and/or the bias of the clutch spring. Another interface (e.g. a splined tooth interface and/or a coupling via a clutch plate) may be provided between the drive sleeve and the number sleeve (or a dose setting component) for rotationally constraining the drive sleeve and the number sleeve depending on the axial position of the drive sleeve. A fifth interface may be provided between the drive sleeve and the rotational strain sensing arrangement for generating a feedback upon the amount of residual rotational strain, preferably only at the end of dose dispensing, and depending on the axial position of the drive sleeve.

In a preferred embodiment, the mechanical reservoir comprises a torsion spring rotationally coupled to the number sleeve. The torsion spring (drive spring) may be pre-strained and/or may be strained (charged) by relative rotation between number sleeve and the housing. The torsion spring may be attached at one end to the housing component and/or an additional housing component and at the other end to a component part coupled to the latch feature. The torsion spring may be pre-wound upon assembly of a drug delivery device, such that it applies a torque to the number sleeve when the mechanism is at zero units dialled.

Providing a resilient drive member, such as a torsion spring, for generating the force or torque required for dose dispensing may reduce the user applied forces for dose dispensing. This may especially become helpful for users with impaired dexterity. In addition, the dial extension of the known manually driven devices, which is a result of the required dispensing stroke, may be omitted by providing the resilient member because merely a small triggering stroke may be necessary for releasing the resilient member.

In a drug delivery device at least one dose setting member may be provided that can be operated to set a dose, wherein actuation of the trigger causes dispensing of the set dose. Preferably, the operation of the at least one dose setting member strains the drive spring and actuation of the trigger allows the drive spring to relax and thereby rotate the number sleeve, the drive sleeve and the lead screw relative to the housing component which causes the lead screw to advance in the distal direction relative to the housing component.

The drug delivery device may further comprise the housing, having a first aperture, the number sleeve positioned within the housing and rotatable with respect to the housing during dose setting and during dose dispensing, and a gauge element, which is interposed between the housing and the number sleeve. Preferably, the gauge element has a second aperture, which is positioned with respect to the first aperture of the housing such that at least a part of the number sleeve is visible through the first and second apertures. The gauge element may be axially guided within the housing and in threaded engagement with the number sleeve such that rotation of the number sleeve causes an axial displacement of the gauge element.

The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the number sleeve, rotation of the number sleeve causes an axial displacement of the gauge element relative to the number sleeve and relative to the housing. The gauge element may have the form of a shield or strip extending in the longitudinal direction of the device. As an alternative, the gauge element may be a sleeve. In an embodiment, the number sleeve is marked with a sequence of numbers or symbols and the gauge element comprises an aperture. With the number sleeve located radially inwards of the gauge element, this allows that at least one of the numbers or symbols on the number sleeve is visible through the aperture or window. In other words, the gauge element may be used to shield or cover a portion of the number sleeve and to allow viewing only on a limited portion of the number sleeve. This function may be in addition to the gauge element itself being suitable for identifying or indicating the actually set and/or dispensed dose.

In a preferred embodiment, the number sleeve, during dose setting, is adapted to undergo a mere rotational movement within the housing and relative to the housing. In other words, the number sleeve does not perform a translational movement during dose setting. This prevents the need for the number sleeve to be wound out of the housing or for the housing to be prolonged for covering the number sleeve within the housing.

It is preferred if the device is suitable for dispensing variable, user-selectable, doses of medicament. The device may be a disposable device, i.e. a device which does not provide for an exchange of an empty cartridge.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. The limiter mechanism may comprise a first rotational stop on the number sleeve and a first counter stop on the gauge element, which abut in the minimum dose (zero) position, and a second rotational stop on the number sleeve and a second counter stop on the gauge element, which abut in the maximum dose position. As the number sleeve rotates relative to the gauge element during dose setting and during dose dispensing, these two components are suitable to form a reliable and robust limiter mechanism.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. In a preferred embodiment, this last dose protection mechanism only detects the medicament remaining in the cartridge when the cartridge contains less than the maximum dose (e.g. 120 IU). For example, the last dose protection mechanism comprises a nut member interposed between the drive member and a component which rotates during dose setting and dose dispensing. The component which rotates during dose setting and dose dispensing may be the number sleeve or a dial sleeve rotationally constrained to the number sleeve. In a preferred embodiment, the number sleeve and/or a dial sleeve rotate during dose setting and during dose dispensing, whereas the drive member only rotates during dose dispensing together with the number sleeve and/or the dial sleeve. Thus, in this embodiment, the nut member will only move axially during dose setting and will remain stationary with respect to these components during dose dispensing. Preferably, the nut member is threaded to the drive member and splined to the number sleeve and/or the dial sleeve. As an alternative, the nut member may be threaded to the number sleeve and/or the dial sleeve and may be splined to the drive member. The nut member may be a full nut or a part thereof, e.g. a half nut.

The injection device may comprise more than one clicker mechanism for generating a tactile and/or audible feedback. During dose setting re-engagement of the clutch features of the (drive) sleeve and the corresponding clutch features of the clutch element may generate an audible and/or tactile feedback. For example, a tactile feedback during dose dispense may be provided by ratchet features located on the trigger and interacting at least during dose dispensing with a clicker arm located on the clutch element. As the clutch element rotates relative to the trigger during dispense, this relative rotation may be used to generate a feedback signal. Preferably, the trigger is rotationally locked to the housing or housing component during dose dispensing.

Preferably, the piston rod (lead screw) advances by a fixed displacement for each revolution of the movable (drive) sleeve. In other embodiments, the rate of displacement may vary. For example, the lead screw may advance a large displacement per revolution to dispense a first amount of medicament from the cartridge and then a smaller displacement per revolution to dispense the rest of the cartridge. This is advantageous, as it can compensate for the fact that the first dose dispensed from the cartridge often has a lower volume than other doses, for a given displacement of the mechanism. If the pitch is equal on the threads of the housing and the lead screw, the lead screw advances a fixed amount for every revolution of the movable sleeve. However, if in an alternative embodiment the first turn of the thread on the lead screw has a large pitch and the other turns have a small pitch, during the first revolution the lead screw displacement depends on the large pitch of the first turn of thread on the lead screw, so it displaces a large amount per revolution. For subsequent revolutions the lead screw displacement depends on the smaller pitch of the lead screw thread, so it displaces a smaller amount. If, in a further embodiment, the housing thread has a larger pitch than the lead screw, during the first revolution, the lead screw displacement depends on the pitch of the housing thread, so it displaces a large amount per revolution. For subsequent revolutions the lead screw displacement depends on the pitch of the lead screw thread, so it displaces a smaller amount.

The aperture in the housing and/or the aperture in the gauge element may be a simple opening. However, it is preferred if at least one aperture is closed by a window or lens which prevents intrusion of dirt and/or may increase legibility of e.g. numbers on the number sleeve, for example due to a magnification.

According to an embodiment the number sleeve is clipped to the housing at the distal end. This reduces the geometric tolerances for the gauge position. In other words, the number sleeve is preferably axially fixed relative to the housing but allowed to rotate relative thereto.

Preferably, the drive sleeve is clipped inside the number sleeve to retain it during subsequent assembly steps. In an alternative embodiment, the drive sleeve is clipped to the housing instead to retain it during subsequent assembly steps. In both embodiments, the drive sleeve is free to move beyond its assembled position when the trigger is pressed. The clips prevent movement in the disassembly direction, but do not prevent further movement, e.g. for dispense.

The lens and the window in the gauge may be incorporated into the housing using a 'twin-shot' moulding technology. For example, they are moulded during a 'first shot' in a translucent material, and the outer cover of the housing is moulded during a 'second shot' in an opaque material.

If there is only one threaded portion on the gauge element this reduces the length of this component.

Preferably, the tooth geometry on the clutch plate and the drive sleeve is chosen such that the dialling torque is low. Further, the clutch plate may comprise a dispense clicker which interferes with clicker teeth on the trigger.

The drug delivery device may comprise a cartridge containing a liquid medicament formulation. The term "medicament" or "medicament formulation", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Non-limiting, exemplary embodiments will now be described with reference to the accompanying drawings, in which:

FIG. 6 shows an interface between the housing and the trigger of the device of FIG. 1;

FIGS. 7a, b show an interface between the number sleeve and the drive sleeve of the device of FIG. 1 in the dose setting mode and in the dose dispensing mode;

FIG. 8 shows an interface between the lead screw and a bearing of the device of FIG. 1;

FIG. 9 shows an interface between the clutch plate and the trigger of the device of FIG. 1;

FIG. 10 shows in a sectional view the components of an end of dose clicker of the device of FIG. 1;

FIGS. 11a-c show in enlarged views the sequence of generating a click at the end of dose dispensing of the device of FIG. 1;

DETAILED DESCRIPTION

Figure 1:
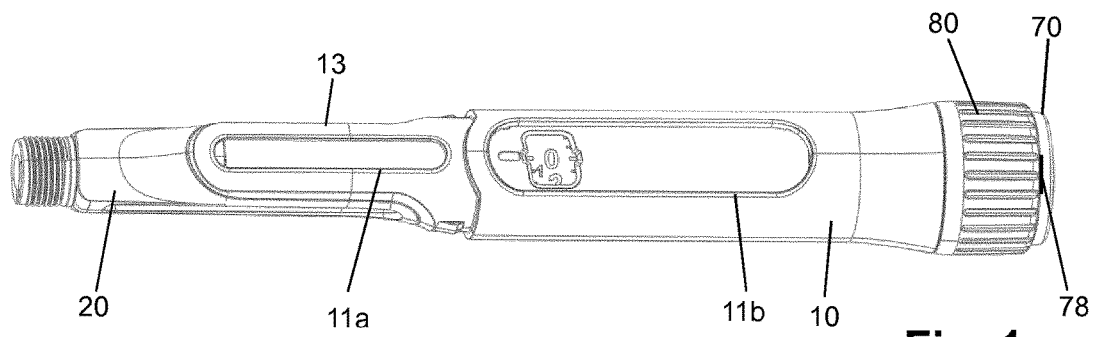
FIG. 1 shows a top view of a first embodiment of a drug delivery device in the minimum dose position.
Figure 2:
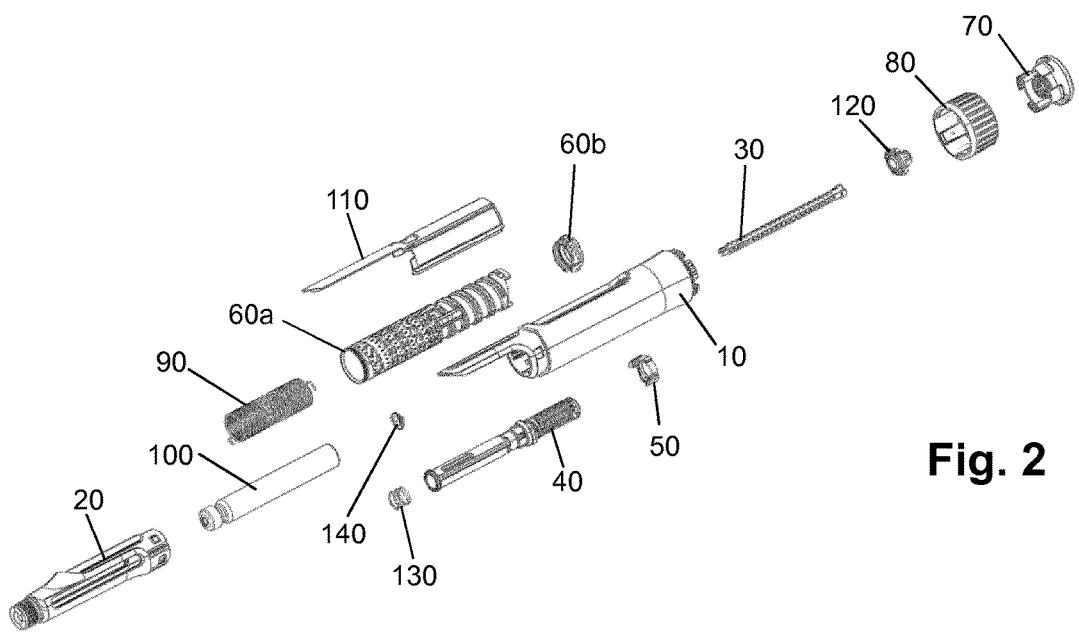
FIG. 2 shows an exploded view of the components of the device of FIG. 1.
Figure 3:
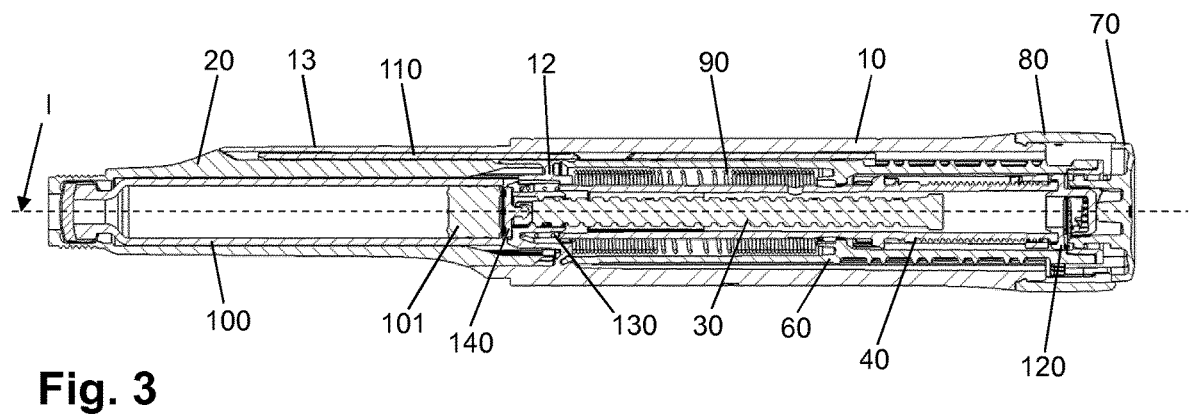
FIG. 3 shows a sectional view of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a trigger in form of a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis I of the mechanism which is shown in FIG. 3.

The housing 10 or body is a generally tubular element having a proximal end with an enlarged diameter. The housing 10 provides location for the cartridge 100 comprising a liquid medicament formulation and cartridge holder 20, windows 11a, 11b for viewing the dose number on the number sleeve 60 and the gauge element 110, and a feature on its external surface, e.g. a circumferential groove, to axially retain the dose selector 80 forming an end stop limiter. A flange-like or cylindrical inner wall 12 of the housing 10 comprises an inner thread engaging the lead screw 30. The housing 10 further has at least one internal, axially orientated slot or the like for axially guiding the gauge element 110. In the embodiment shown in the Figures, the distal end is provided with an axially extending strip 13 partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The lead screw 30 is rotationally constrained to the drive sleeve 40 via a splined interface. When rotated, the lead screw 30 is forced to move axially relative to the drive sleeve 40, through its threaded interface with the inner wall 12 of housing 10 forming a threaded nut.

The lead screw 30 is an elongate member with an outer thread 31 (FIG. 4a) engaging the corresponding thread of the inner wall 12 of housing 10. The thread 31 may have a large lead-in, for example a wedge shape form, at its distal end to engage a corresponding housing thread form on the first rotation. At its distal end (see FIG. 8), the lead screw 30 is provided with an interface for clip attachment of the bearing 140. In the present embodiment, this interface comprises two clip arms 32 extending in the distal direction defining an insertion space between them for insertion of a bearing 140 interface. As an alternative, the interface may comprise only one single clip arm extending more than 180° about the longitudinal axis, or may comprise one or several clip arms 32. The clip arm(s) 32 may have a bent form with a recessed clip portion as shown in FIG. 8. Preferably, the clip arm(s) form a cylindrical outer face having a diameter equal to or smaller than the outer diameter of the lead screw 30 at the base of the groove (flute base) of the outer thread 31. A concave contact surface 33 is provided between the clip arms 32 for abutment of a corresponding portion of bearing 140 (convex contact surface 143).

The injection device provides a drive train comprising the drive sleeve 40 which is a hollow member surrounding the lead screw 30 and arranged within number sleeve 60. It extends from an interface with the clutch plate 120 to the contact with the clutch spring 130. The drive sleeve 40 is axially movable relative to the housing 10, the lead screw 30 and the number sleeve 60 in the distal direction against the bias of clutch spring 130 and in the opposite proximal direction under the bias of clutch spring 130.

The lead screw 30 comprises a longitudinal (axial) groove 35 which forms a splined connection with a longitudinal (axial) spline 49 of the drive sleeve 40 in order to rotationally constrict the lead screw 30 to the drive sleeve 40 but to allow axial movement of the lead screw 30 with regard to the drive sleeve 40. The groove 35 is also referred to as rotational input interface whereas the spline 49 forms a downstream interface of the drive sleeve.

Figure 18:
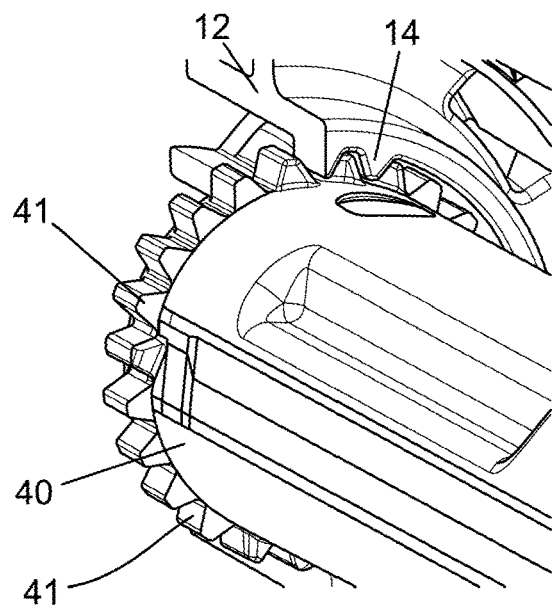
FIG. 18 shows an interface between the housing and the drive sleeve of the device of FIG. 1.

A splined tooth interface with the housing 10 (also referred to as releasable latch) prevents rotation of the drive sleeve 40 during dose setting. This interface which is shown in FIG. 18 in detail comprises a ring of radially extending outer teeth 41 at the distal end of drive sleeve 40 and corresponding radially extending inner teeth 14 of the housing component 10. When the button (trigger) 70 is pressed, these drive sleeve 40 to housing 10 spline teeth 14, 41 are disengaged allowing the drive sleeve 40 to rotate relative to housing 10 (for example for dose dispense).

A further splined tooth interface with the number sleeve 60 is not engaged during dialling, but engages when the button 70 is pressed, preventing relative rotation between the drive sleeve 40 and number sleeve 60 during dispense. In the preferred embodiment shown in FIGS. 7a and 7b this interface comprises inwardly directed splines 61 on a flange 62 on the inner surface of the number sleeve 60 and a ring of radially extending outer splines 42 of drive sleeve 40 (the splines 42 are also referred to as upstream interface and the splines 61 are referred to as rotational interface). The corresponding splines 61, 42 are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

Preferably, the splines 61, 42 are arranged such that they are decoupled when teeth 41 of drive sleeve 40 and inner teeth 14 of housing component 10 mesh and engage when teeth 41 and inner teeth 14 disengage. In a preferred embodiment the splines 61, 42 are longer in the axial direction compared with teeth 41, 14. This allows engagement of the splines 61, 42 shortly before disengagement of teeth 41, 14. In other words, the splines 61, 42 and the teeth 41, 14 are designed and arranged such that actuation of the button 70 rotationally constrains the drive sleeve 40 to the number sleeve 60 before the drive sleeve 40 is allowed to rotate relative to housing 10. Similarly, as the button 70 is released after dose dispensing axial movement of the drive sleeve 40 first rotationally constrains the drive sleeve 40 to the housing and thereafter decouples splines 61, 42. As an alternative to the corresponding splines 61, 42 teeth may be provided. As a further alternative or in addition to splines 61, 42, drive sleeve 40 and number sleeve 60 may be rotationally coupled to each other during dose dispensing via clutch plate 120.

Figure 19:
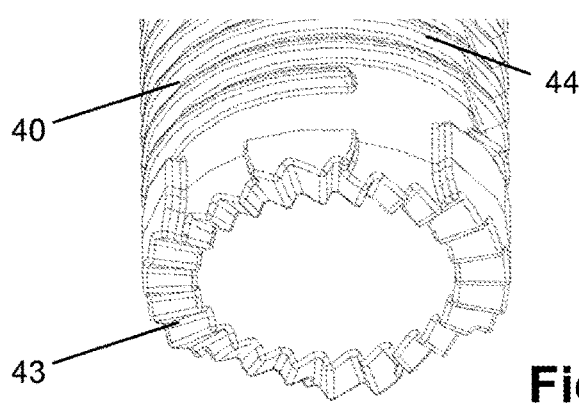
FIG. 19 shows an interface between the clutch plate and the drive sleeve of the device of FIG. 1.

An interface of the drive sleeve 40 which is shown in FIG. 19 comprises a ring of ratchet teeth 43 located at the proximal end face of drive sleeve 40 and a ring of corresponding ratchet teeth 121 of clutch plate 120.

Figure 20:
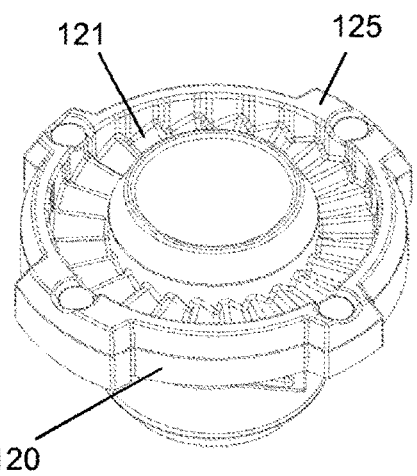
FIG. 20 shows a last dose mechanism of the device of FIG. 1.
Figure 20:
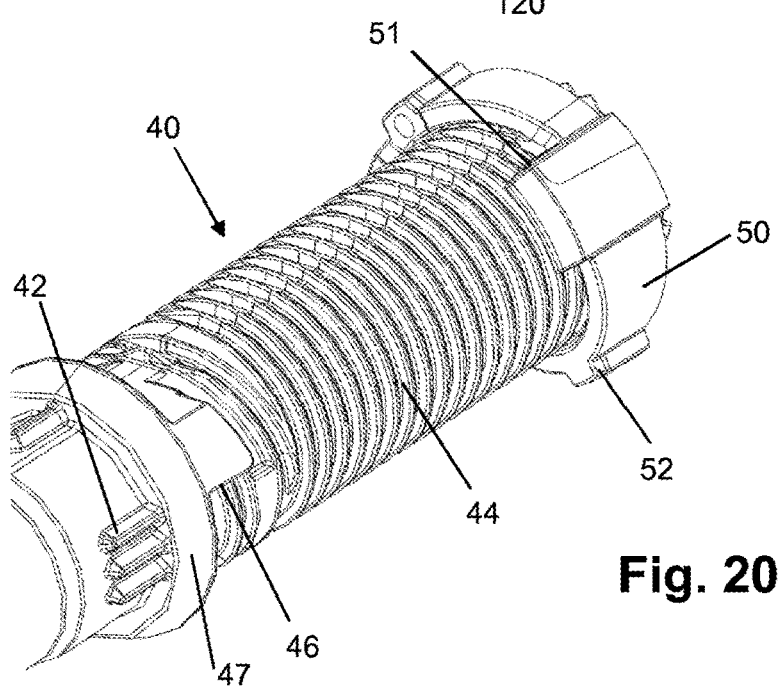

The drive sleeve 40 has a threaded section 44 providing a helical track for the nut 50 (FIG. 20). In addition, a last dose abutment or stop 46 is provided which may be the end of the thread 44 track or preferably a rotational hard stop for interaction with a corresponding last dose stop 51 of nut 50, thus limiting movement of the nut 50 on the thread 44. At least one longitudinal spline 49 engages a corresponding track 35 of the lead screw 30 (FIG. 10). Further, the drive sleeve 40 is provided with a ramp 47 (FIG. 20) interacting with a clicker arm 67 (FIG. 10)9 when the drive sleeve 40 is in its distal position during dose dispensing, i.e. when button 70 is depressed.

The last dose nut 50 is located between the number sleeve 60 and the drive sleeve 40. It is rotationally constrained to the number sleeve 60, via a splined interface (splines 52 on nut 50). It moves along a helical path relative to the drive sleeve 40, via a threaded interface (thread 44), when relative rotation occurs between the number sleeve 60 and drive sleeve 40 which is during dialling only. This is shown in FIG. 20. As an alternative, the nut 50 may be splined to the drive sleeve 40 and threaded to the number sleeve 60. In the embodiment shown in the Figures, the nut 50 is a full nut, but in alternative embodiments it may be a half nut, i.e. a component extending approximately 180° around the center axis of the device. A last dose stop 51 is provided engaging stop 46 of drive sleeve 40 when a dose is set corresponding to the remaining dispensable amount of liquid medicament formulation in the cartridge 100.

The dose indicator or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the opening 11b in the housing 10, to denote the dialled dose of medicament.

Figure 14:
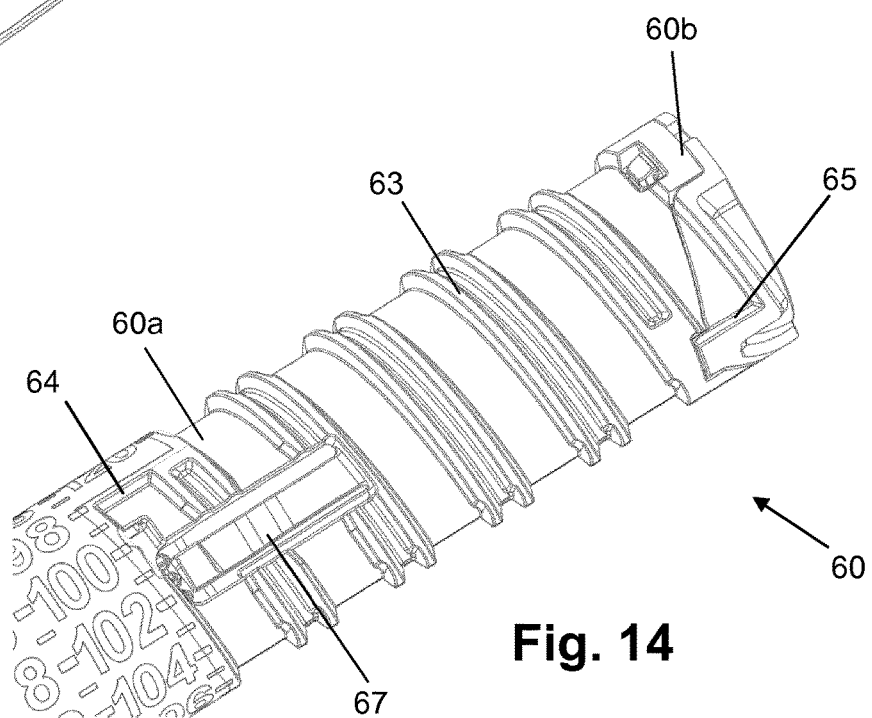
FIG. 14 shows a portion of the number sleeve of the device of FIG. 1.
Figure 15:
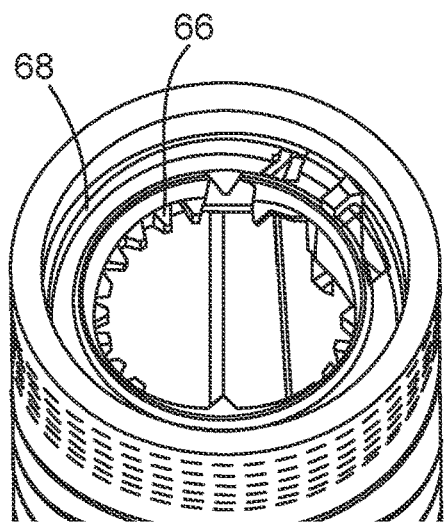
FIG. 15 shows a further portion of the number sleeve of the device of FIG. 1.
Figure 16:
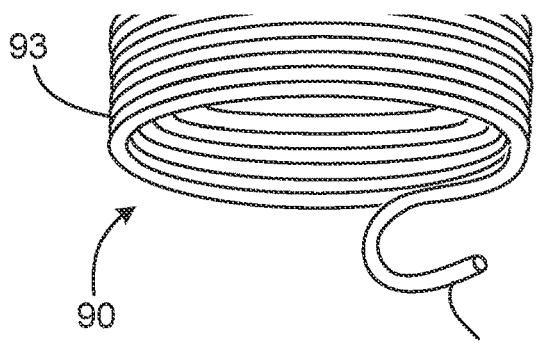
FIG. 16 shows a portion of the drive spring of the device of FIG. 1.

Further, the number sleeve lower 60a has a portion with an outer thread 63 (see FIG. 14) engaging the gauge element 110. End stops 64, 65 are provided at the opposite ends of thread 63 to limit relative movement with respect to the gauge element 110.

Figure 5:
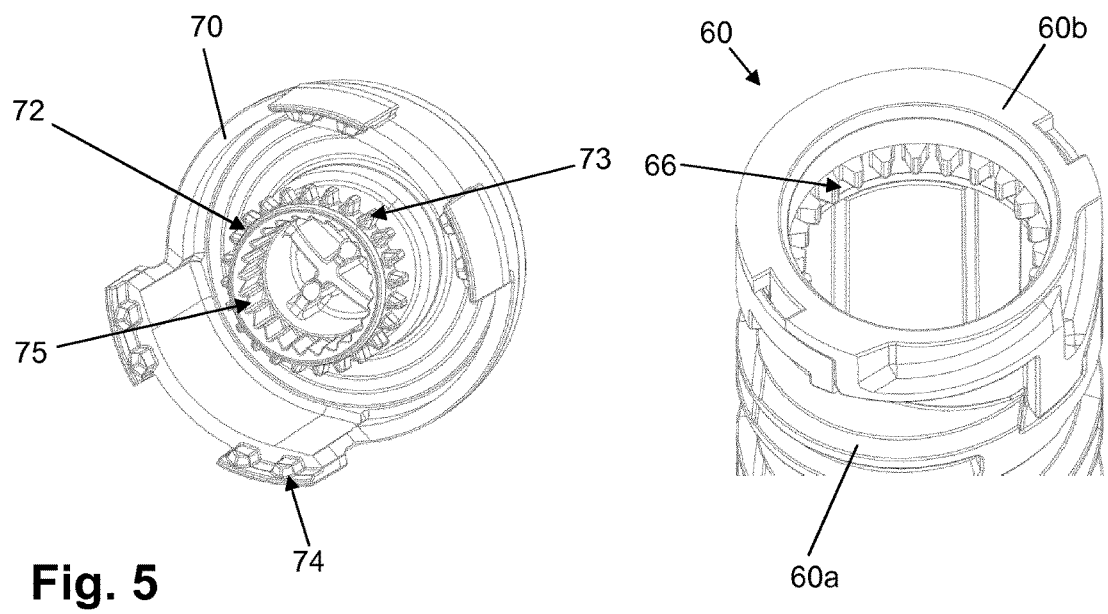
FIG. 5 shows an interface between the number sleeve and the trigger of the device of FIG. 1.

Clutch features which have the form of a ring of splines 66 in the embodiment shown in FIG. 5 are provided inwardly directed on number sleeve lower 60a for engagement with splines 73 of the button 70 during dose setting and dose correction. A clicker arm 67 is provided on the outer surface of number sleeve 60 which interacts with the drive sleeve 40 and the gauge member 110 for generating a feedback signal. In addition, the number sleeve lower 60a is rotationally constrained to the nut 50 and to the clutch plate 120 via a splined interface comprising at least one longitudinal spline at its inner surface.

An interface for attachment of the torsion spring 90 to the number sleeve lower 60a comprises large lead-ins and a groove feature with a pocket or anchor point for receiving a first coil or hook portion of the spring. The groove has an end feature in the form of a ramp that is in interference with the hook portion 91 of the spring. The design of the groove is such that the spring 90 may be received within the pocket without interfering with the gauge element 110. The mechanical energy reservoir for driving the lead screw 30 during dose dispensing comprises the number sleeve 60 and the torsion spring 90.

The button (trigger) 70 which forms the proximal end of the device is permanently splined to the dose selector 80. A central stem 71 (see FIG. 4b) extends distally from the proximal actuation face of the button 70. The stem 71 is provided with a flange 72 carrying the splines 73 for engagement with splines 66 of the number sleeve upper 60b (FIG. 5). Thus, it is also splined via splines 66, 73 (FIG. 5) to the number sleeve upper 60b when the button 70 is not pressed, but this spline interface is disconnected when the button 70 is pressed. The button 70 has a discontinuous annular skirt with splines 74. When the button 70 is pressed, splines 74 on the button 70 engage with splines on the housing 10 (FIG. 6), preventing rotation of the button 70 (and hence the dose selector 80) during dispense. These splines 74, 15 disengage when the button 70 is released, allowing a dose to be dialled. Further, a ring of ratchet teeth 75 is provided on the inner side of flange 72 (FIG. 9) for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

Figure 21:
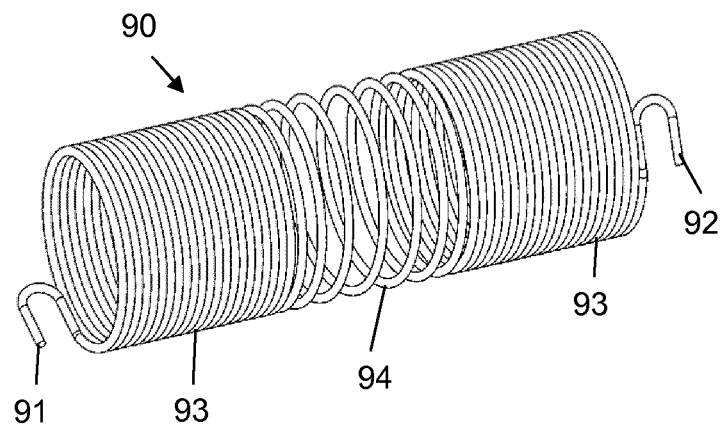
FIG. 21 shows the torsion spring of the device of FIG. 1.

The torsion spring 90 is attached at its distal end to the housing 10 and at the other end to the number sleeve 60. The torsion spring 90 is located inside the number sleeve 60 and surrounds a distal portion of the drive sleeve 40. As shown in FIG. 21, the spring has a hook 91 at one end for attachment on the number sleeve 60. A similar hook end 92 is provided at the opposite end for attachment on the housing 10. The torsion spring 90 is pre-wound upon assembly, such that it applies a torque to the number sleeve 60 when the mechanism is at zero units dialled. The action of rotating the dose selector 80, to set a dose, rotates the number sleeve 60 relative to the housing 10, and charges the torsion spring 90 further.

The torsion spring 90 is formed from a helical wire with at least two different pitches. In FIG. 21, both ends are formed from 'closed' coils 93, i.e. the pitch equals the wire diameter and each coil contacts the adjacent coil. The central portion has 'open' coils 94, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is for example a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

Figure 13:
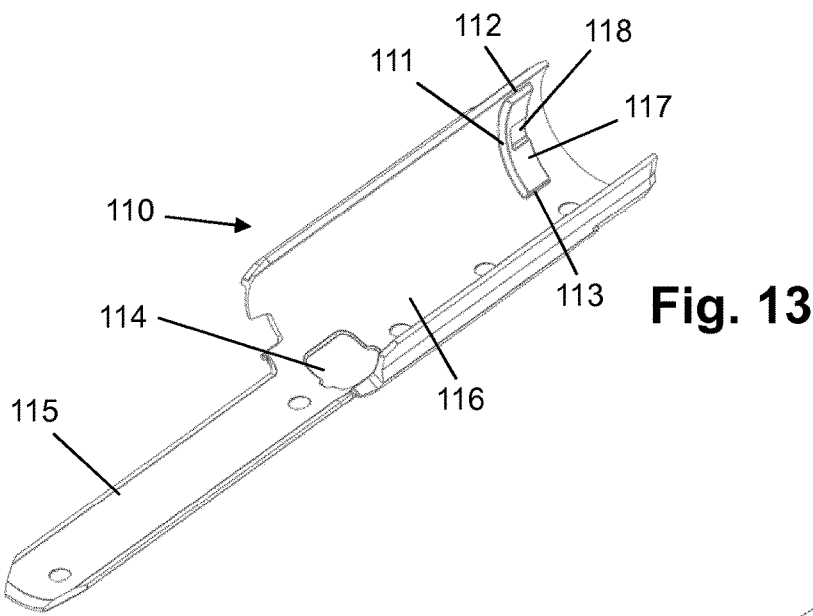
FIG. 13 shows the gauge element of the device of FIG. 1.

The gauge element 110 (FIG. 13) is constrained to prevent rotation but allow translation relative to the housing 10 via a splined interface. The gauge element 110 has a helical feature 111 on its inner surface which engages with the helical thread 63 cut in the number sleeve 60 such that rotation of the number sleeve 60 causes axial translation of the gauge element 110. This helical feature on the gauge element 110 also creates stop abutments 112, 113 against the end stop 64, 65 of the helical cut in the number sleeve 60 to limit the minimum and maximum dose that can be set.

The gauge element 110 has a generally plate or band like component having a central aperture 114 or window and two flanges 115, 116 extending on either side of the aperture. The flanges 115, 116 are preferably not transparent and thus shield or cover the number sleeve 60, whereas the aperture 114 or window allows viewing a portion of the number sleeve lower 60a. Further, gauge element 110 has a cam 117 and a recess 118 (FIGS. 11a-12c) interacting with the clicker arm 67 of the number sleeve 60 at the end of dose dispensing.

As can be seen in FIGS. 9 and 19, the clutch plate 120 is a sleeve-like or ring-like component. The clutch plate 120 is splined to the number sleeve 60 via outer splines 125. It is also coupled to the drive sleeve 40 via a ratchet interface (ratchet teeth 43, 121). The ratchet provides a detent position between the number sleeve 60 and drive sleeve 40 corresponding to each dose unit, and engages different ramped tooth angles during clockwise and anti-clockwise relative rotation. A clicker arm 123 is provided on the clutch plate 120 for interaction with ratchet features 75 of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface (ratchet teeth 43, 121) is always engaged. In the 'at rest' position, it also ensures that the button splines 73 are engaged with the number sleeve splines 66, and the drive sleeve teeth 41 are engaged with teeth 14 of the housing 10.

The bearing 140 (see FIG. 8) is axially constrained to the lead screw 30 and acts on the bung 101 within the liquid medicament cartridge. It is axially clipped to the lead screw 30, but free to rotate. The bearing 140 comprises a disc 141 having a stem 142 extending in the proximal direction. The stem 142 has at its proximal end a convex contact surface 143. In addition, a recessed portion 144 is provided on the stem 142. The curvature of the convex contact surface 143 and the concave contact surface 33 of the lead screw 30 is chosen such that the contact diameter between the bearing 140 and lead screw 30 is small to minimize the frictional losses at this interface. The design of the clip interface between bearing 140 and lead screw 30 permits the lead screw 30 to be assembled axially, from the proximal end and through the thread engagement to the housing 10, which simplifies assembly. In addition, this design allows a simple "open and shut" mould tooling for both components.

Figure 4A:
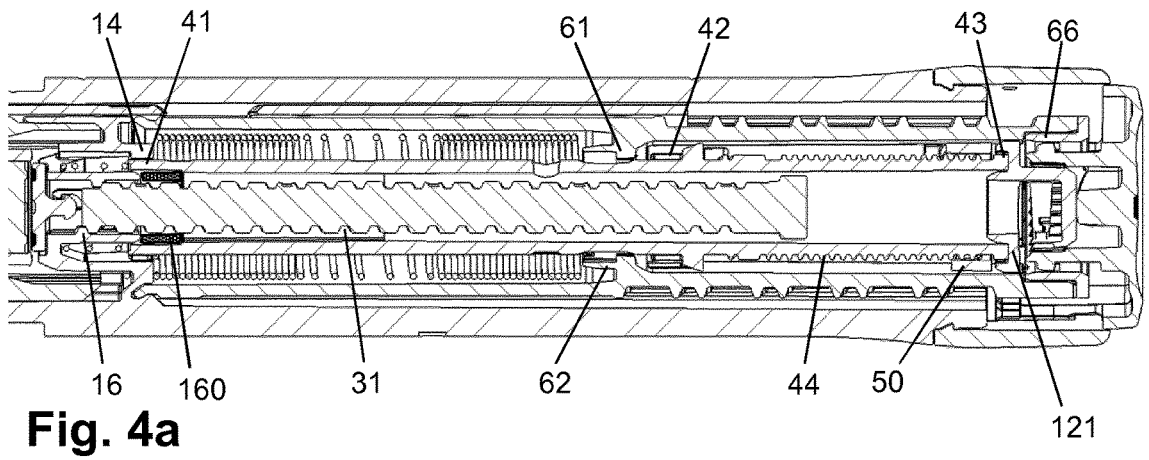
FIG. 4a shows an enlarged sectional view of a detail of the device of FIG. 1 in the dose setting mode.
Figure 17A:
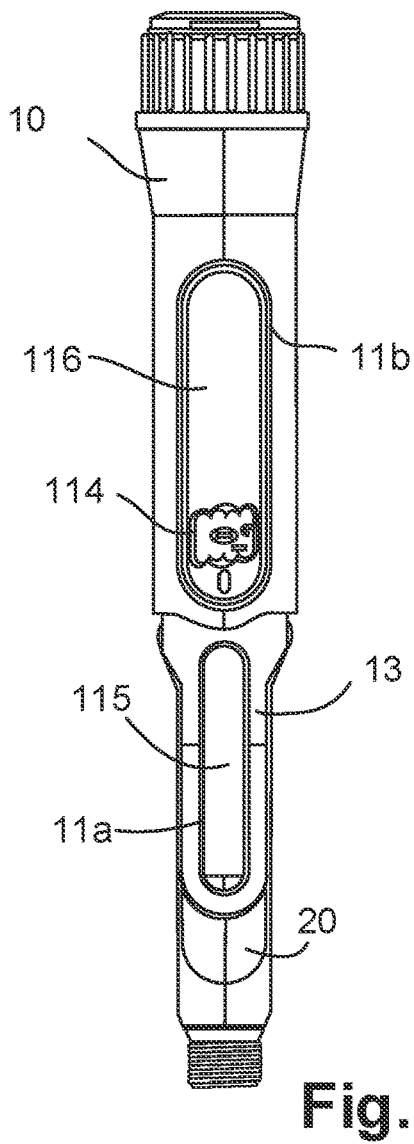
FIGS. 17a, b show top views of the device of FIG. 1 with 0 units dialled and with 96 units dialled.

With the device in the 'at rest' condition as shown in FIGS. 4a and 17a, the number sleeve 60 is positioned against its zero dose abutment 64, 113 with the gauge element 110 and the button 70 is not depressed. Dose marking '0' on the number sleeve 60 is visible through the windows 11b and 114 of the housing 10 and gauge element 110, respectively.

The torsion spring 90, which has a number of pre-wound turns applied to it during assembly of the device, applies a torque to the number sleeve 60 and is prevented from rotating by the zero dose abutment 64, 113. It is also possible to 'back-wind' the mechanism slightly due to an offset between the zero dose stop 64, 113 and the angular offset of the drive sleeve 40 spline teeth. This has the effect of preventing possible weeping when a dose is dialled and the zero dose abutment is disengaged.

The automated assembly of the torsion spring 90 into the number sleeve 60 can be achieved by incorporating large lead-ins and a groove feature to the number sleeve 60. As the torsion spring 90 is rotated during assembly, the hook end form 91 locates in the groove feature before engaging the anchor point in the number sleeve 60. To help to prevent the torsion spring 90 disengaging the anchor point during subsequent assembly steps it is possible to create an interference between the torsion spring 90 and the number sleeve 60, or a one-way clip feature.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges 115, 116 either side of the window area 114 which cover the numbers printed on the number sleeve 60 adjacent to the dialled dose to ensure only the set dose number is made visible to the user (see FIGS. 17a and 17b).

A specific feature of this disclosure is the inclusion of a visual feedback feature in addition to the discrete dose number display typical on devices of this type. The distal end, namely flange 115, of the gauge element 110 creates a sliding scale through a small window 11a in the housing 10 (see FIGS. 17a and 17b). As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

Figure 17B:
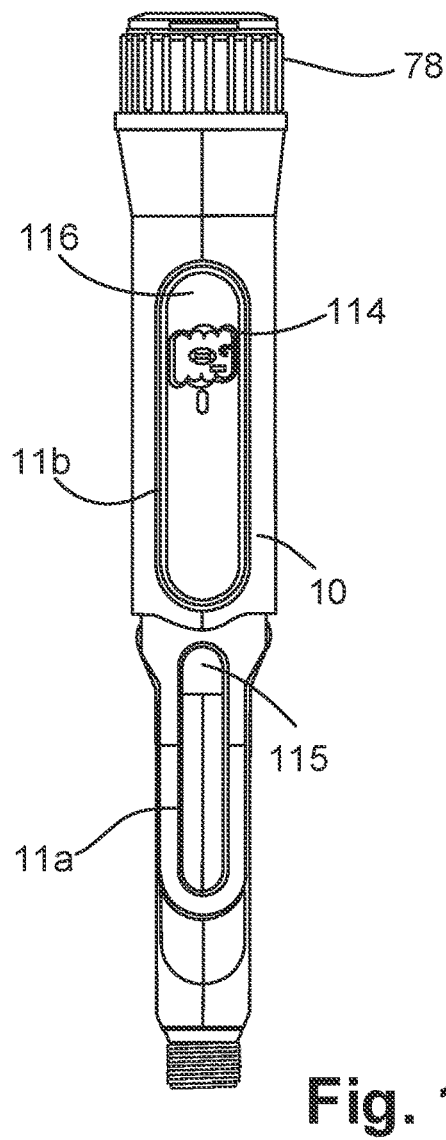

The openings 11a, 11b in the housing 10 allow the user to view the gauge feature and number display as shown in FIGS. 17a and 17b. To reduce dust ingress and prevent the user from touching moving parts, these openings 11a, 11b are covered by translucent windows. These windows may be separate components, but in this embodiment they are incorporated into the housing 10 using 'twin-shot' moulding technology. A first shot of translucent material forms the internal features and the windows 11a, 11b, and then a 'second shot' of opaque material forms the outer cover of the housing 10.

The mechanism utilises a dose selector 80 with an increased diameter relative to the housing 10 which aids dialling although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth 41 with teeth 14 of the housing 10. Relative rotation must therefore occur between the clutch plate 120 and drive sleeve 40 via the ratchet interface 43, 121.

The user torque required to rotate the dose selector 80 is a sum of the torque required to wind up the torsion spring 90, and the torque required to overhaul the ratchet interface 43, 121. The clutch spring 130 is designed to provide an axial force to the ratchet interface 43, 121 and to bias the clutch plate 120 onto the drive sleeve 40. This axial load acts to maintain the ratchet teeth engagement of the clutch plate 120 and drive sleeve 40. The torque required to overhaul the ratchet 43, 121 in the dose set direction is a function of the axial load applied by the clutch spring 130, the clockwise ramp angle of the ratchet teeth 43, 121, the friction coefficient between the mating surfaces and the mean radius of the ratchet interface 43, 121.

As the user rotates the dose selector 80 sufficiently to increment the mechanism by one increment, the number sleeve 60 rotates relative to the drive sleeve 40 by one ratchet tooth. At this point the ratchet teeth 43, 121 re-engage into the next detent position. An audible click is generated by the ratchet re-engagement, and tactile feedback is given by the change in torque input required.

Relative rotation of the number sleeve 60 and the drive sleeve 40 is allowed as splines 42, 61 are disengaged during dose setting. This relative rotation also causes the last dose nut 50 to travel along its threaded path, towards its last dose abutment at last dose stop 46 on the drive sleeve 40.

With no user torque applied to the dose selector 80, the number sleeve 60 is now prevented from rotating back under the torque applied by the torsion spring 90, solely by the ratchet interface 43, 121 between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface 43, 121 between the number sleeve 60 and drive sleeve 40 is repeated for each dose increment. Additional energy is stored within the torsion spring 90 for each dose increment and audible and tactile feedback is provided for each increment dialled by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment 65 on the maximum dose abutment 112 of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment 51 with stop face 46 of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface 43, 121 between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines 74 on the button 70 engage with splines 15 on the housing 10, preventing rotation of the button 70 (and hence the dose selector 80) during dispense. As the button 70 is stationary during dispense, it can be used in the dispense clicker mechanism as shown in FIG. 9. A stop feature in the housing 10 limits axial travel of the button 70 and reacts any axial abuse loads applied by the user, reducing the risk of damaging internal components.

Figure 4B:
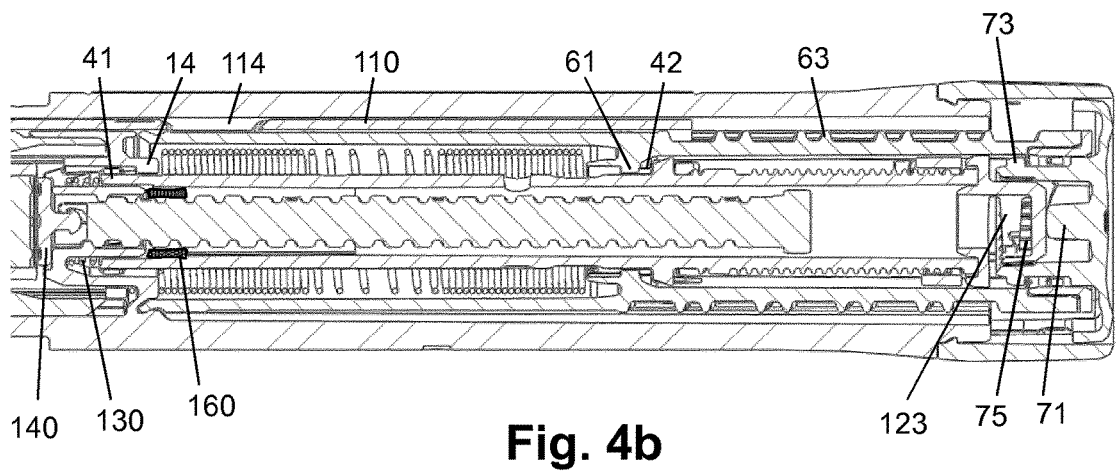
FIG. 4b shows an enlarged sectional view of a detail of the device of FIG. 1 in the dose dispensing mode.

The clutch plate 120 and drive sleeve 40 travel axially with the button 70. This engages the splined tooth interface 42, 61 between the drive sleeve 40 and number sleeve 60 as shown in FIGS. 4b and 7b (splines 42, 61 engaged), preventing relative rotation between the drive sleeve 40 and number sleeve 60 during dispense (in contrast, in FIGS. 4a and 7a splines 42, 61 are engaged). The splined tooth interface 41, 14 between the drive sleeve 40 and the housing 10 disengages (see FIG. 4b), so the drive sleeve 40 can now rotate and is driven by the torsion spring 90 via the number sleeve 60, and clutch plate 120.

Rotation of the drive sleeve 40 causes the lead screw 30 to rotate due to their splined engagement, and the lead screw 30 then advances due to its threaded engagement to the housing 10. The number sleeve 60 rotation also causes the gauge element 110 to traverse axially back to its zero position whereby the zero dose abutment 64, 113 stops the mechanism.

The bearing 140 is axially clipped to the lead screw 30, but free to rotate. Since the bearing 140 is in direct contact with the bung 101, it does not rotate as the lead screw 30 rotates and advances during dose dispense. As described above, the contact diameter between the bearing 140 and lead screw 30 is small to minimise the frictional losses at this interface. The design of the lead screw 30 and bearing 140 eliminates delicate clip features or large contact diameters present on previous concepts. This embodiment also allows the lead screw 30 to be assembled axially, from the proximal end and through the thread engagement to the housing 10, which simplifies assembly.

Tactile feedback during dose dispense is provided via the compliant cantilever clicker arm 123 integrated into the clutch plate 120. This arm 123 interfaces radially with ratchet features 75 on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features 75 engage with the clicker arm 123 to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines 14, 41 between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialling only.

Once the delivery of a dose is stopped, by the number sleeve 60 returning to the zero dose abutment, the user may release the button 70, which will re-engage the spline teeth 14, 41 between the drive sleeve 40 and housing 10. The mechanism is now returned to the 'at rest' condition.

It is possible to angle the spline teeth 14, 41 on either the drive sleeve 40 or housing 10 so that when the button 70 is released the re-engagement of the spline teeth 14, 41 fractionally 'backwinds' the drive sleeve 40 thereby removing the engagement of the number sleeve 60 to the zero dose stop abutment on the gauge element 110. This compensates for the effect of clearances in the mechanism (for example due to tolerances) which could otherwise lead to slight advancement of the lead screw 30 and medicament dispense when the device is dialled for the subsequent dose due to the number sleeve 60 zero dose stop not restraining the mechanism and instead the restraint returning to the splines between the drive sleeve 40 and housing 10.

At the end of dose dispensing, additional audible feedback is provided in the form of a 'click', distinct from the 'clicks' provided during dispense, to inform the user that the device has returned to its zero position via the interaction of the clicker arm 67 on the number sleeve 60 with the ramp 47 on the drive sleeve 40 and the cam 117 and the recess 118 on the gauge element 110. This embodiment allows feedback to only be created at the end of dose delivery and not created if the device is dialled back to, or away from, the zero position.

FIG. 11a shows the position of the click features when the device is in the 'at rest' condition, with zero units dialled and the button 70 not depressed. It can be seen that the cam feature 117 on the gauge element 110 does not contact the clicker arm 67 on the number sleeve 60 when the button 70 is in the 'at rest' condition, so during storage or dialling the clicker arm 67 is not deflected.

During dialling, the gauge element 110 translates in the proximal direction, so the cam 117 is no longer aligned axially with the clicker arm 67. At the start of dose delivery when the drive sleeve 40 translates in the distal direction, the ramp 47 on the drive sleeve 40 pushes the clicker arm 67 radially outwards. During dose delivery, the gauge element 110 translates back in the distal direction, and towards the end of dose delivery, the clicker arm 67 contacts the cam 117 on the gauge element 110. For small doses, the cam 117 and clicker arm 67 will be in contact at the start of the dose. FIGS. 11b to 12c show the component interactions. After dose delivery, the button 70 is released and the end of dose mechanism returns to its 'at rest' position.

In FIG. 11b a dose is dialled and approximately one full dial turn is applied to number sleeve 60. Gauge element 110 is axially translated away from zero unit position, so that cam 117 is no longer aligned axially with clicker arm 67. FIG. 11c shows the start of dispensing, when button 70 is depressed to initiate dose dispense and which causes the drive sleeve 70 to translate axially. Ramp 47 on the drive sleeve 40 pushes clicker arm 67 radially out and into radial alignment with cam 117 on the gauge element 110.

Figure 12A:
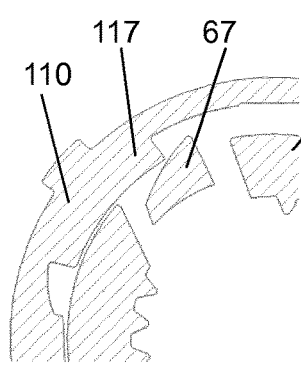
FIGS. 12a-c show in enlarged sectional views the sequence of generating a click at the end of dose dispensing of the device of FIG. 1.
Figure 12B:
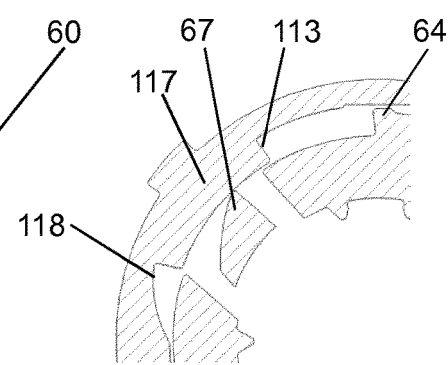
Figure 12C:
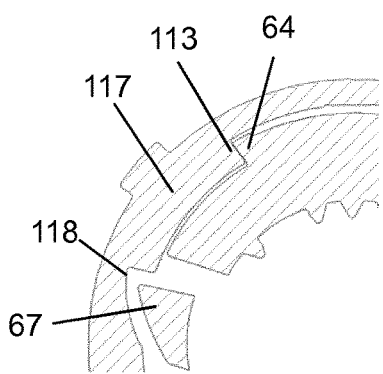

FIG. 12a shows the mechanism at the end of dose dispensing with approximately 4 units remaining. The gauge element 110 returns axially towards its zero unit position, so that cam 117 aligns axially with clicker arm 67. Rotation of number sleeve 60 causes clicker arm 67 to contact cam 117 such that clicker arm 67 is pushed radially inwards. With approximately 2 units remaining the number sleeve 60 rotates further and clicker arm 67 follows the profile of cam 117 (FIG. 12b). This radial deflection 'charges' clicker arm 67 storing elastic energy. In FIG. 12c dispensing is completed as the number sleeve 60 reaches its zero unit rotational position. The clicker arm 67 drops off the sharp edge of cam 117 into recess 118. Elastic energy is released causing clicker arm 67 to spring radially outwards to contact cam 117 and create a distinct 'click'.

In the principal embodiment, the lead screw 30 advances by a fixed displacement for each revolution of the drive sleeve 40. In other embodiments, the rate of displacement may vary. For example, the lead screw 30 may advance a large displacement per revolution to dispense a first amount of medicament from the cartridge 100 and then a smaller displacement per revolution to dispense the rest of the cartridge 100. This is advantageous, as it can compensate for the fact that the first dose dispensed from the cartridge 100 often has a lower volume than other doses, for a given displacement of the mechanism.

Figure 22:
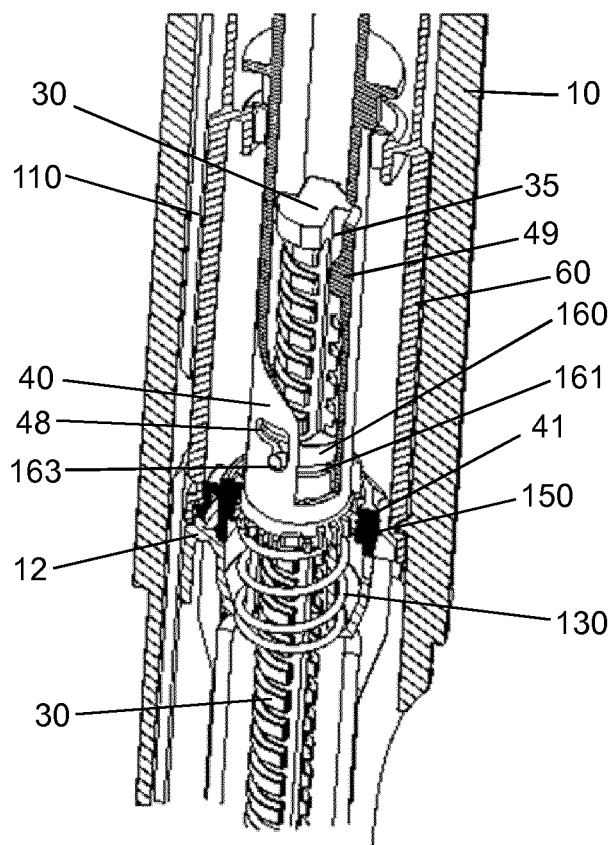
FIG. 22 shows an enlarged sectional view of a detail of the device of FIG. 1 in the zero dose position and in the dose dialling mode.
Figure 23:
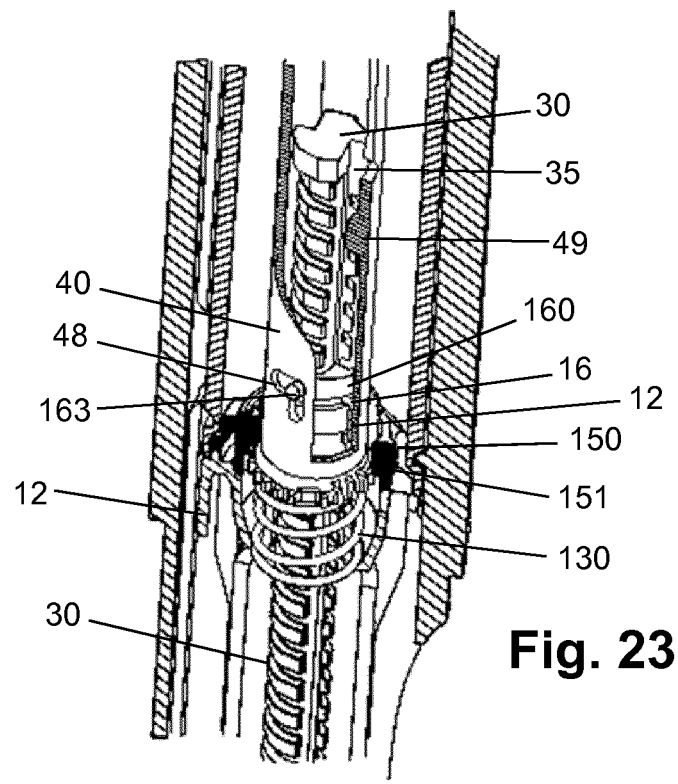
FIG. 23 shows the enlarged sectional view of FIG. 22 in the dose dispensing mode (first step)
Figure 24:
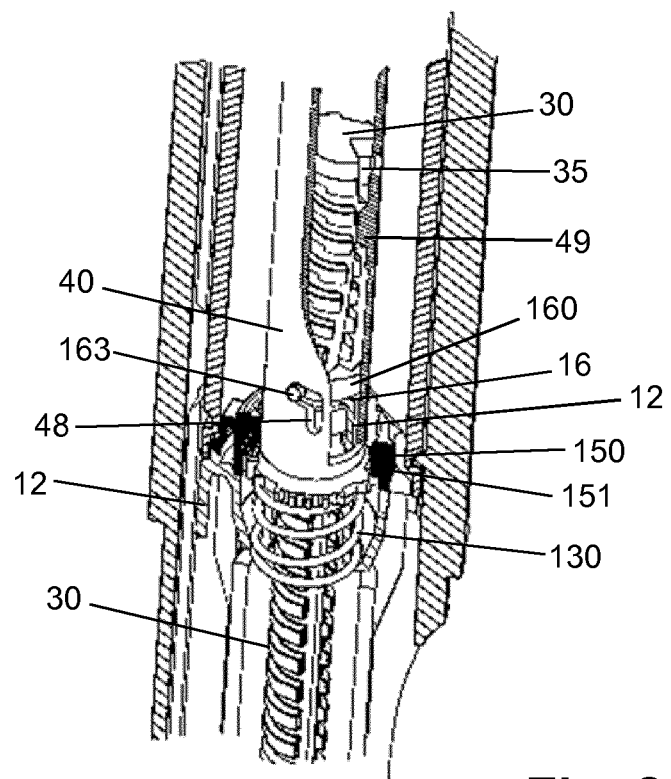
FIG. 24 shows the enlarged sectional view of FIG. 22 in the dose dispensing mode (second step)

Using FIGS. 22 to 24 an embodiment communicating to the user that the needle is blocked is described in more detail with regard to a drug delivery device comprising above features. It is therefore referred to the above Figures and explanation as well as reference numbers. The drug delivery device only differs with regard to the housing which now comprises two components, the housing 10 and a body insert 150. The body insert 150 comprises a ring of teeth 151 which corresponds to the ring of teeth 14 of the housing 10 shown in FIGS. 1 to 21. The ring- or sleeve-like body insert 150 is fixedly attached to the housing 10. The embodiments described below may likewise be realized with a two-part housing 10, 150 as described and shown in FIGS. 22 to 27 or with a one-part (integral) housing 10 as described in FIGS. 1 to 21.

As indicated above the drug delivery device comprises rotational strain sensing arrangement comprising a locking ring 160 which is axially constrained within the flange like inner wall 12 of the housing 10 but free to rotate relative to the housing 10. For that the locking ring 160 comprises a groove 161 at the outer surface of the locking ring 160. The groove 161 cooperates with a radial projection 16 provided at the proximal end of the inner wall 12 (see FIG. 24). The locking ring 160 is accommodated within the drive sleeve 40 at its distal end. The lead screw 30 is axially movable within the locking ring 160 by means of a splined connection, the drive sleeve 40 rotates together with the locking ring 160 during dose dispensing. The locking ring 160 further comprises a radial pin 163 projecting from its outer surface and accommodated within an L-shaped track (e.g. slot) 48 within the drive sleeve 40 at its distal end. The L-shaped track 48 comprises a first axial section and a second section (horizontal section) perpendicular to the longitudinal axis I of the drug delivery device. The L-shaped track 48 goes through the drive sleeve 40.

The spline connection between the drive sleeve 40 and the lead screw 30 comprising the spline 49 and the groove 35 is located an appreciable distance from the locking ring 160.

After initiating delivery of a medicament dose by depressing the button 70 moving the button 70 from a first extended position to a second retracted position the drive sleeve 40 is moved distally to disengage its teeth 41 from the body insert 150 clutch teeth 151. This moves the locking ring 160 locking pin 163 within the L-shaped track 48 along the first section so that it is located in the 'elbow' of the L-shaped track 48. This is shown in FIG. 23.

In the alternative embodiment in which the housing is integrally formed in the retracted position of the button 70 the drive sleeve 40 is disengaged from the clutch teeth 14 as indicated above.

Once the drive sleeve 40 is released from the body insert 150 or the housing 10, the dispensing torque of the torsion spring 90 is transferred to the lead screw 30. The lead screw 30 will then deflect in a twisting fashion along the section between the body thread and the drive sleeve splines, over which the torque is applied. This twisting motion causes the drive sleeve 40 and with it the L-shaped track 48 to rotate until the locking ring 160 locking pin 163 is at the end of the second horizontal section (see FIG. 24).

In this state, the drive sleeve 40 is prevented from returning to its proximal starting position under the action of the clutch spring 130 even if the button 70 is released. The components will remain in this state until transfer of torque from the torsion (drive) spring 90 is stopped by the engagement of the 0 unit stop features.

So, if the drug delivery device reaches the 0 unit stop, but the needle is blocked and torsion remains in the mechanism, the button 70 will remain in its depressed position providing feedback to the user that the needle is blocked. If the device does not reach the 0 units as a result of a blocked needle, the button 70 will also remain in its depressed position, but the dose display will also not have returned to 0 providing additional feedback that the dose has not been completed.

Figures 30, 31:
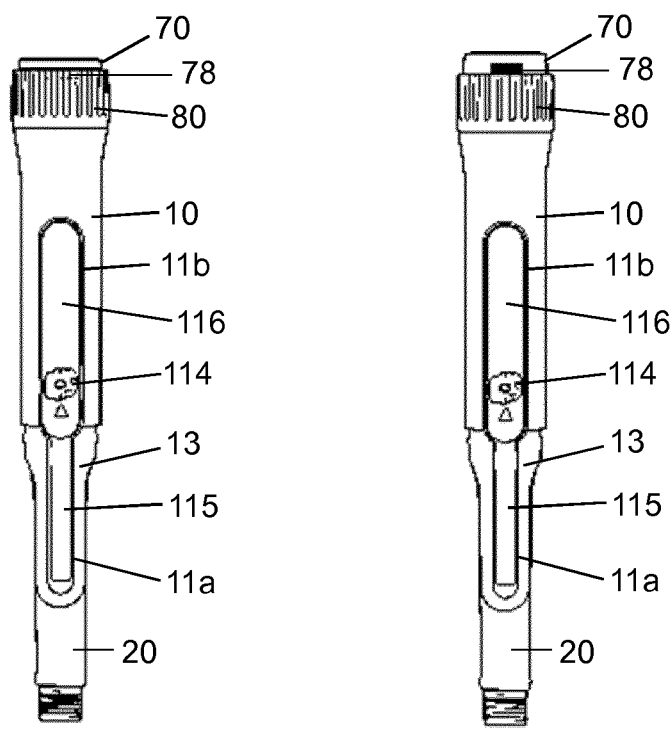
FIG. 30 shows a top view of the device of FIG. 1 after dose dispensing showing blocked needle.
FIG. 31 shows a top view of the device of FIG. 1 after dose dispensing showing correct injection with no residual torque.

To help the clarity of feedback provided by the button position, a flag or other feature, for example a colored marking (flag) 78 as shown in FIG. 31, for example, may be provided at the outer surface of the button 70. If torsion remains in the mechanism, the button 70 keeps its retracted second position as shown in FIG. 30 and the flag 78 is hidden by the dose selector 80. The user easily derives the status of the device from that. If the flag 78 is visible, the user knows that the dose delivery was finished correctly (see FIG. 31).

In a blocked needle condition, even though the drive sleeve 40 will not actively push the button 70 back to its first extended (proximal) position, if the device is held upside down, it may be possible that the button 70 could fall to its second position. To prevent this, a detent feature may be added between the button 70 and the dose selector 80 that was sufficient to resist the weight of the button 70 but not sufficient to resist the force of the clutch spring 130 (applied to the button 70 via the drive sleeve 40 and clutch plate 120). With this feature, the button 70 would only return to its first position when driven by the drive sleeve 40 (via the clutch plate 120) in an unblocked needle condition.

Figure 25:
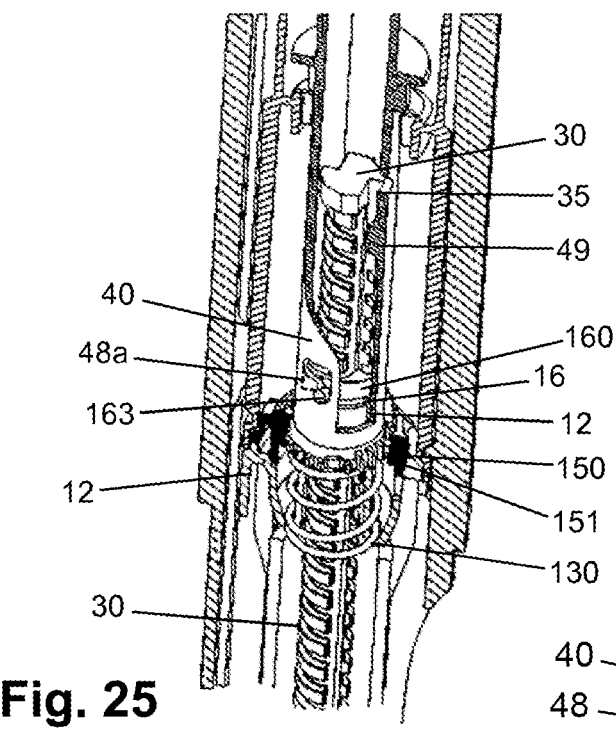
FIG. 25 shows an enlarged sectional view of a detail of a second embodiment of a drug delivery device in the zero dose position and in the dose dialling mode.

In another embodiment shown in FIG. 25 it may be desirable to allow the user to interrupt the dispense action of the drug delivery device part way through dispense by removing the distally acting axial force that they apply to the button 70.

In this embodiment, if the user removes the force from the button 70, the drive sleeve re-engages the body insert 150 clutch teeth 151 (or teeth 14 of the housing 10), causing it to stop rotating and the drug delivery device to stop dispensing. In the embodiment explained with regard to FIGS. 22 to 24 above, the drive sleeve 40 is held in the distal position even if the button 70 is released (by the L-shaped track 48). In this distal position, the drive sleeve 40 cannot re-engage the body insert 150 clutch teeth 151 and dispense is likely to continue.

In contrast, in the embodiment shown in FIG. 25, the second horizontal section of the L-shaped track 48 is widened (see dashed line 48a in FIG. 25), i.e. has a higher width into the axial direction of the drug delivery device, allowing the drive sleeve 40 to move proximally at the moment the pressure to the button 70 is reduced until it starts to engage the body insert 150 clutch teeth 151 and stopping dispense but preventing it from returning completely to its starting position, so that the user feedback regarding a blocked needle condition is maintained.

Figure 26:
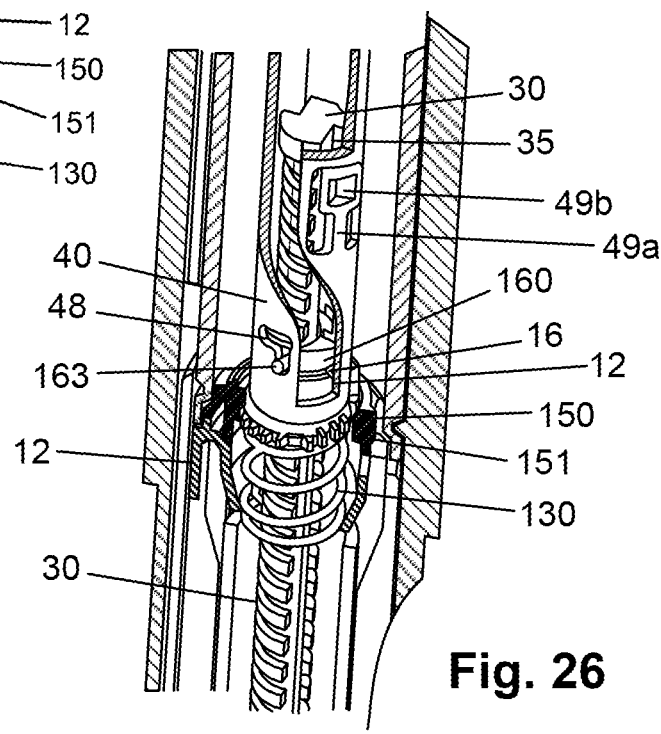
FIGS. 26,26a show an enlarged sectional view of a detail of a third embodiment of a drug delivery device in the zero dose position and in the dose dialling mode.
Figure 26A:
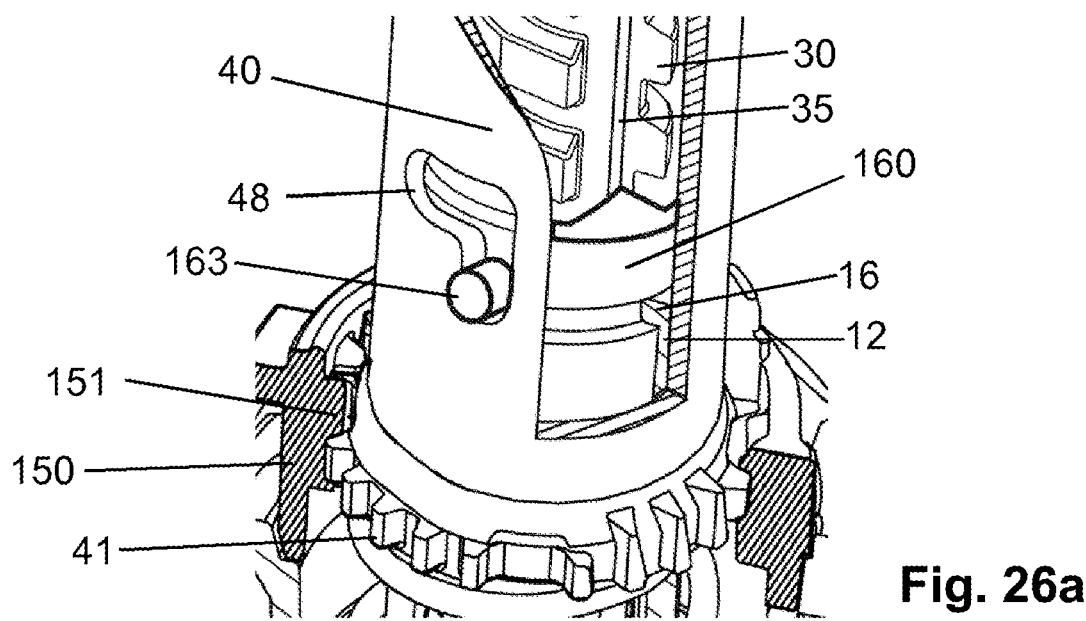
Figure 27:
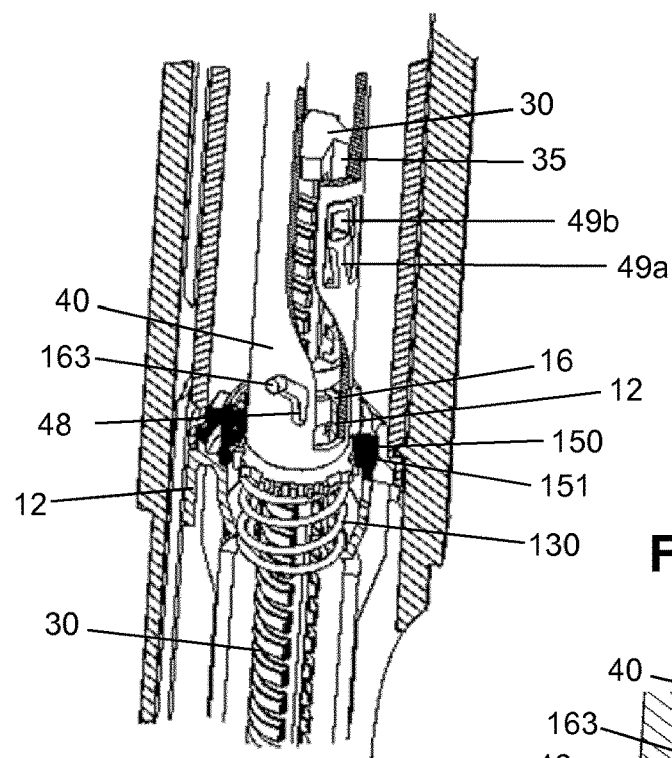
FIGS. 27,27a show the enlarged sectional view of FIG. 26 in the dose dispensing mode.
Figure 27A:
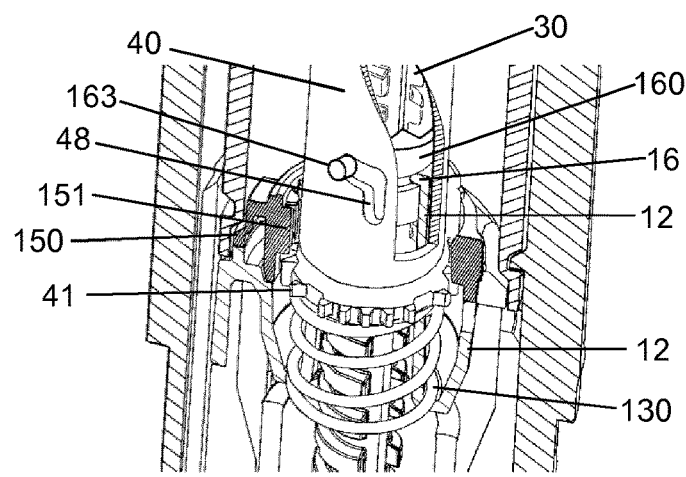

The principle of operation of another embodiment shown in FIGS. 26 to 27 is very similar to that of the embodiment explained with regard to FIGS. 22 to 25. The key difference is that the flexibility of the lead screw 30, required to achieve relative rotation between the locking ring 160 and drive sleeve 40, and causing engagement of the horizontal section of the L-shaped track 48, is replaced by flexibility of at least one flexible arm 49a on the drive sleeve 40. The arm 49a extends along the longitudinal direction l within the plane of the drive sleeve 40 and comprises a spline feature 49b that engages the lead screw 30 via the axial groove 35. The spline feature 49b extends from the inner surface of the flexible arm 49a and the drive sleeve 40. The flexible arm 49a may be formed by a cutout within the drive sleeve 40.

As shown in FIG. 27 the flexible arm 49a is twisted in a tangential direction (perpendicular to the longitudinal direction l) caused by torque of torsion spring 90. Thereby the mechanism is made more reliable. With regard to the operation of this embodiment it is referred to the embodiment explained with regard to FIGS. 22 to 24 wherein the lead screw twisting is replaced by twisting of the flexible arm 49a. The button 70 cannot return to its first extended position as long as there is residual torque in the system which twists flexible arm 49a.

Figure 28:
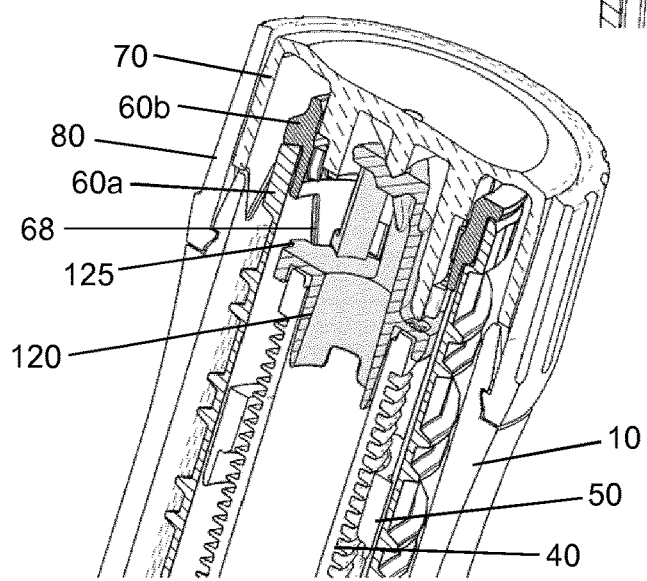
FIG. 28 shows an enlarged sectional view of a detail at the proximal end of a fourth embodiment of a drug delivery device in the dose dispensing mode.
Figure 29:
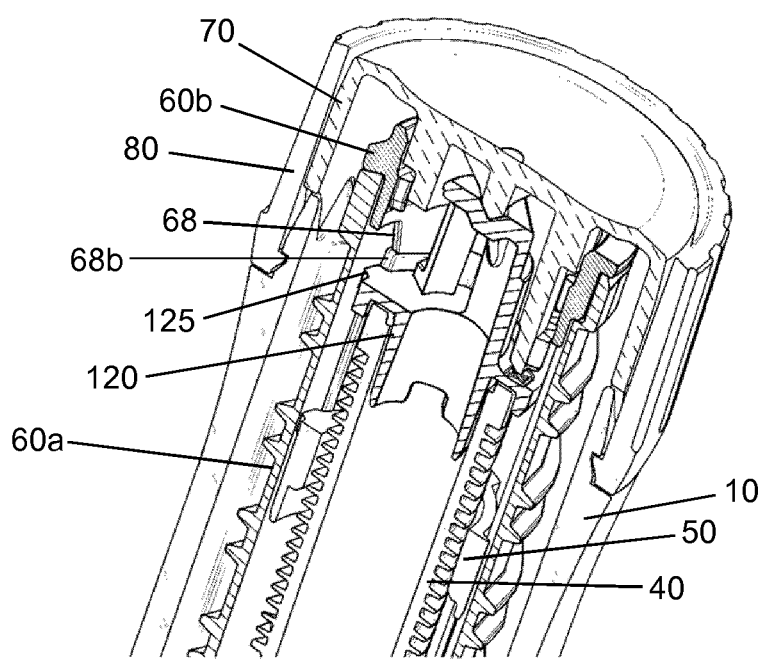
FIG. 29 shows an enlarged sectional view of a detail at the proximal end of a fifth embodiment of a drug delivery device in the dose dispensing mode.

Another embodiment is depicted in FIG. 28. In this embodiment there is no body insert and no L-shaped track within the drive sleeve 40. In contrast, in this embodiment the torsional load path that exists during dispense (and remains loaded at the end of the dose if a blocked needle is fitted) passes from the number sleeve lower 60a to the clutch plate 120. When a dose is dispensed, the clutch plate 120 is moved distally relative to the number sleeve lower 60a, but the components remain in splined engagement. In this embodiment, the side of the number sleeve spline surface 68 that transfers the torsion to the clutch plate 120 is formed by the number sleeve upper 60b (which is rigidly connected to the number sleeve lower 60a so that together they functionally form a single component) and has an angled surface.

As long as sufficient torsion is applied between the number sleeve upper 60b and the clutch plate 120 via this number sleeve angled spline surface 68, the resulting axial load is sufficient to react the axial force from the clutch spring 130. This causes the clutch plate 120 to be held in the distal position and thereby prevents the clutch spring 130 from returning the button 70 to the first position even if the button 70 is released by the user, as long as torsion remains within the mechanism. The flag 78 at the button 70 remains hidden by the dose selector 80 showing that there is some problem with the drug delivery device and dose dispense was not finished correctly. This button retention mechanism alerts the user to the fact that the needle is blocked in the same way as the previously described embodiments. The button 70 is only returned to its first extended position by the clutch spring 130 if the torque in the system is released.

Alternatively, in the fifth embodiment the user is allowed to interrupt dose dispensing by removing the force they apply to the button 70. In this embodiment, the spline in the number sleeve 60 that transfers the torque to the clutch plate 120 during dispense is no longer purely formed as angled surface on the number sleeve upper 60b only. Instead, it is partially formed by an angled spline surface 68 on the number sleeve upper 60b and partially formed by a spline surface 68b on the number sleeve lower 60a that runs at least parallel to the longitudinal axis of the drug delivery device. The number sleeve lower 60a spline surface 68b may alternatively be formed with the opposite angle to the number sleeve upper 60b spline surface 68, relative to the longitudinal axis. Therefore (whether the surface 68b is parallel to the axis of the device or oppositely angled), when the device is dispensing and this interface is loaded, if the user releases force from the button 70, the clutch plate 120 is allowed to move proximally until it contacts the angled surface of the number sleeve upper 60b. This movement is sufficient to allow the drive sleeve 40 to engage the body insert 150 and stop dispense, but is not sufficient to return the button 70 to its fully proximal position, i.e. the first position, so that the user would still be made aware that the needle is blocked, for example by viewing the flag 78.

REFERENCE NUMERALS 10 housing
11a, b opening
12 flange-like inner wall
13 strip
14 teeth
15 spline
16 radial projection of inner wall
20 cartridge holder
30 lead screw (piston rod)
31 outer thread
32 clip arm
33 concave contact surface
35 longitudinal groove
40 driver (axially movable drive sleeve)
41 teeth
42 spline
43 ratchet teeth
44 threaded section
46 last dose stop
47 ramp
48 L-shaped track
48a widened L-shaped track
49 spline
49a flexible arm
49b spline feature
50 nut (last dose nut)
51 last dose stop
52 spline
60 dose indicator (number sleeve)
60a number sleeve lower
60b number sleeve upper
61 spline
62 flange
63 outer thread
64, 65 end stop
66 spline
67 clicker arm
68 angled spline surface of number sleeve upper 60b
68b angled spline surface of number sleeve lower 60a
70 button
71 stem
72 flange
73, 74 spline
75 ratchet teeth
78 flag
80 dose selector
90 torsion spring
91, 92 hook
93, 94 coil
100 cartridge
101 bung
110 gauge element
111 helical feature
112, 113 stop
114 aperture
115, 116 flange
117 cam
118 recess
120 clutch plate
121 ratchet teeth
123 clicker arm
125 clutch plate spline
130 clutch spring
140 bearing
141 disc
142 stem
143 convex contact surface
144 recessed portion
150 body insert
151 teeth
160 locking ring
161 groove
163 radial pin
l longitudinal axis
R direction of revolution

The invention claimed is:

1. A drug delivery device for expelling a pre-determined or pre-settable amount of a liquid medicament formulation, the drug delivery device comprising:
a medicament reservoir attached to a housing; and
an expelling mechanism configured for acting against the medicament reservoir in order to expel a portion of the liquid medicament formulation therefrom, the expelling mechanism comprising:
an arrangement of a threaded nut in a fixed axial relation to the housing and a lead screw in threaded engagement with the threaded nut, the threaded nut and the lead screw being rotatable relative to each other by a rotational input interface,
a mechanical energy reservoir for storing energy, the energy being releasable from the mechanical energy reservoir by a rotational interface,
a drive train having an upstream interface coupled to the rotational interface of the mechanical energy reservoir for feeding rotational energy into the drive train and a downstream interface coupled to the rotational input interface of the arrangement of the threaded nut and the lead screw for outputting rotational energy thereto to thereby rotate the lead screw and the threaded nut relative to each other, the drive train further being equipped with a releasable latch for preventing transfer of rotational energy from the upstream interface to the downstream interface when actuated and for allowing transfer of rotational energy from the upstream interface to the downstream interface when released, and a trigger movable relative to the housing from a first position to a second position, the trigger being connected to the releasable latch for operating the releasable latch, and the trigger further being biased towards the first position opposite to the second position corresponding to release of the releasable latch, wherein the drive train further comprises a rotational strain sensing arrangement which is configured to convert rotational strain into an axial force or an interlocking, the axial force or the interlocking being applied to the trigger by a mechanical linkage to thereby prevent the trigger from returning to the first position until the rotational strain acting on the rotational strain sensing arrangement of the drive train is reduced below a predetermined threshold value.

2. The drug delivery device according to claim 1, wherein the mechanical linkage between the trigger and the rotational strain sensing arrangement is configured to allow the trigger to leave the second position under any torque strain condition and to move towards an intermediate position away from the second position thereby causing re-engagement of the releasable latch.

3. The drug delivery device according to claim 1, wherein the releasable latch is located between the upstream interface and the rotational strain sensing arrangement or wherein the releasable latch is located between the downstream interface and the rotational strain sensing arrangement.

4. The drug delivery device according to claim 1, wherein the drive train further includes a user-settable end stop limiter configured for enabling a user to restrict an amount of rotation that is transferred by the drive train upon release of the releasable latch to a user-determined angle.

5. The drug delivery device according to claim 4, wherein the mechanical energy reservoir is coupled to the user-settable end stop limiter to translate setting of the end stop limiter into immediate energizing of the energy reservoir to an extent corresponding to the user-determined angle.

6. The drug delivery device according to claim 1, wherein the first position of the trigger is an extended position with respect to the housing.

7. The drug delivery device according to claim 6, wherein the second position is a retracted position with respect to the housing.

8. The drug delivery device according to claim 1, wherein the drive train comprises a drive sleeve and the downstream interface of the drive train comprises a spline at the drive sleeve, a first splined connection formed by the spline (49, 49b) and the rotational input interface being located at an axial distance relative to the threaded nut, wherein the rotational strain sensing arrangement includes a locking ring being maintained in a rotational fixed relation to the lead screw by a second splined connection at a position located between the first splined connection and the threaded nut, the locking ring and the drive sleeve implementing angular dependent axial keying to thereby limit relative axial travel between the locking ring and the drive sleeve when an advancing angle of the drive sleeve relative to the threaded nut due to torsional deformation exceeds a predefined threshold angle.

9. The drug delivery device according to claim 8, wherein the torsional deformation occurs in a flexible arm on the drive sleeve and/or in the lead screw.

10. The drug delivery device according to claim 8, wherein the mechanical linkage between the trigger and the rotational strain sensing arrangement includes a mechanical connection that at least partially limits travel of the trigger according to the limitation occurring in an angular dependent axial keying between the drive sleeve and the threaded nut (12).

11. The drug delivery device according to claim 10, wherein the trigger is mechanically connected to an axial movement of the drive sleeve and/or to the threaded nut.

12. The drug delivery device according to claim 8, wherein the angular dependent axial keying comprises a slotted engagement of a radial pin rotationally fixed at the locking ring and the drive sleeve in an L-shaped track to thereby restrict relative axial travel between the threaded nut and the drive sleeve according a relative angular position thereof.

13. The drug delivery device according to claim 12, wherein a second section of the L-shaped track allows a movement of the radial pin in an axial direction.

14. The drug delivery device according to claim 1, wherein the rotational strain sensing arrangement of the drive train comprises a helical interface for converting the rotational strain into an axial strain.

15. The drug delivery device according to claim 14, wherein the mechanical linkage between the rotational strain sensing arrangement and the trigger is configured to feed an axial force produced by the rotational strain sensing arrangement to the trigger to thereby compensate a biasing force until the rotational strain acting on the rotational strain sensing arrangement of the drive train reduces below the predetermined threshold value.

16. The drug delivery device according to claim 14, wherein the helical interface comprises a clutch plate having an outer spline and a proximal section of a number sleeve having an inner spline, wherein at least one of the outer spline and the inner spline has an angled surface or edge, and wherein the clutch plate is axially coupled to the trigger.

17. The drug delivery device according to claim 16, wherein the angled surface or edge of the inner spline comprises a first inner spline section formed by the proximal section of the number sleeve.

18. The drug delivery device according to claim 17, wherein the angled surface or edge of the inner spline further comprises a second inner spline section formed by a distal section of the number sleeve.

19. The drug delivery device according to claim 1, further comprising the liquid medicament formulation, the liquid medicament formulation being contained within the medicament reservoir.

20. The drug delivery device according to claim 1, further comprising the housing to which the medicament reservoir is attached.

* * * * *